(12) United States Patent
Garg et al.

(10) Patent No.: US 12,009,107 B2
(45) Date of Patent: Jun. 11, 2024

(54) SEASONALLY ADJUSTED PREDICTIVE DATA ANALYSIS

(71) Applicant: Optum, Inc., Minnetonka, MN (US)

(72) Inventors: Siddharth Garg, New Delhi (IN); Jyoti Nahata, Chennai (IN); Madhuri Yadav, Gurgaon (IN); Danita Kiser, Marietta, GA (US); Prashant Singh, Noida (IN); Aishwarya Aishwarya, Gurgaon (IN)

(73) Assignee: Optum, Inc., Minnetonka, MN (US)

( * ) Notice: Subject to any disclaimer, the term of this patent is extended or adjusted under 35 U.S.C. 154(b) by 931 days.

(21) Appl. No.: 17/015,531

(22) Filed: Sep. 9, 2020

(65) Prior Publication Data

US 2022/0076848 A1  Mar. 10, 2022

(51) Int. Cl.
*G16H 50/80* (2018.01)
*G06N 5/04* (2023.01)
*G06N 20/00* (2019.01)

(52) U.S. Cl.
CPC ............ *G16H 50/80* (2018.01); *G06N 5/04* (2013.01); *G06N 20/00* (2019.01)

(58) Field of Classification Search
CPC .......... G16H 50/80; G06N 20/00; G06N 5/04
USPC ........................................................... 703/6
See application file for complete search history.

(56) References Cited

U.S. PATENT DOCUMENTS

| 10,318,874 | B1 * | 6/2019 | Duncan | G06N 20/00 |
| 10,783,399 | B1 * | 9/2020 | Bruno | G06F 16/45 |
| 10,936,947 | B1 * | 3/2021 | Flunkert | G06N 3/044 |
| 11,120,361 | B1 * | 9/2021 | Januschowski | G06N 20/00 |
| 11,126,660 | B1 * | 9/2021 | Sen | G06N 3/044 |
| 11,281,969 | B1 * | 3/2022 | Rangapuram | G06N 7/01 |
| 11,509,715 | B2 * | 11/2022 | Rafey | G06N 20/00 |

(Continued)

OTHER PUBLICATIONS

Song et al. ("Time series analysis of influenza incidence in Chinese provinces from 2004 to 2011", Medicine (2016), pp. 1-7) (Year: 2016).*

(Continued)

*Primary Examiner* — Iftekhar A Khan
(74) *Attorney, Agent, or Firm* — ALSTON & BIRD LLP

(57) ABSTRACT

There is a need for more effective and efficient seasonally-adjusted predictive data analysis solutions. This need can be addressed by, for example, solutions for performing seasonally-adjusted predictive data analysis that use autoregressive integrated moving average (ARIMA) machine learning models. In one example, a method includes: identifying a seasonally-adjusted training input timeseries data object and a seasonally-adjusted testing timeseries data object; generating a trained ARIMA machine learning model using the seasonally-adjusted training input timeseries data object; determining a validation determination for the trained ARIMA machine learning model based on the seasonally-adjusted testing timeseries data object; determining whether the validation determination describes a positive validation; and in response to determining that the validation determination describes the positive validation, enabling performance of a predictive inference using the trained ARIMA machine learning model in order to generate one or more prospective time-lagged predictions and to perform prediction-based actions based on the prospective time-lagged predictions.

20 Claims, 12 Drawing Sheets

(56) References Cited

U.S. PATENT DOCUMENTS

| | | | | |
|---|---|---|---|---|
| 11,551,124 | B2* | 1/2023 | Singh | G06N 20/10 |
| 11,630,928 | B2* | 4/2023 | Rajendran | G06F 30/20 |
| | | | | 703/2 |
| 11,663,493 | B2* | 5/2023 | Shashikant Rao | G06N 5/01 |
| | | | | 706/13 |
| 2009/0319295 | A1* | 12/2009 | Kass-Hout | G16H 50/80 |
| | | | | 707/999.102 |
| 2013/0132572 | A1* | 5/2013 | Pan | H04W 4/029 |
| | | | | 709/225 |
| 2016/0234078 | A1* | 8/2016 | Jana | H04L 47/30 |
| 2017/0070414 | A1* | 3/2017 | Bell | H04L 43/16 |
| 2017/0116530 | A1* | 4/2017 | Modarresi | G06Q 10/04 |
| 2019/0354836 | A1* | 11/2019 | Shah | G06N 3/045 |
| 2020/0065667 | A1* | 2/2020 | Agarwal | G06N 7/01 |
| 2020/0097810 | A1* | 3/2020 | Hetherington | G06N 20/20 |
| 2020/0242134 | A1* | 7/2020 | Salhin | G06F 16/906 |
| 2020/0364618 | A1* | 11/2020 | Peh | G06Q 10/0635 |
| 2021/0011830 | A1* | 1/2021 | Khokhar | G06F 3/0632 |
| 2021/0295189 | A1* | 9/2021 | Singh | G06N 20/10 |
| 2021/0296007 | A1* | 9/2021 | Singh | G16H 50/80 |
| 2021/0342691 | A1* | 11/2021 | Lui | G06N 3/045 |
| 2021/0357402 | A1* | 11/2021 | Cheng | G06Q 30/0202 |
| 2021/0390423 | A1* | 12/2021 | Latapie | H04L 41/0631 |
| 2022/0059230 | A1* | 2/2022 | Muse | G16H 50/70 |
| 2022/0083897 | A1* | 3/2022 | Saha | G06F 16/2477 |
| 2022/0108453 | A1* | 4/2022 | Ajri | G06F 30/23 |

OTHER PUBLICATIONS

Baquero et al. ("Dengue forecasting in São Paulo city with generalized additive models, artificial neural networks and seasonal autoregressive integrated moving average models",Plos One, 2018. pp 1-12) (Year: 2018).*

Chujai et al. ("Time Series Analysis of Household Electric Consumption with ARIMA and ARMA Models", IMECS 2013, pp. 1-6) (Year: 2013).*

Petukhova et al. ("Assessment of autoregressive integrated moving average (ARIMA), generalized linear autoregressive moving average (GLARMA), and random forest (RF) time series regression models for predicting influenza A virus frequency in swine in Ontario, Canada", Plos One, 2018, pp. 1-17) (Year: 2018).*

Tran et al. ("Seasonal-adjustment Based Feature Selection Method for Predicting Epidemic with Large-scale Search Engine Logs", arXiv, 2020, pp. 1-10) (Year: 2020).*

Biggerstaff, Matthew et al. "Results From The Second Year Of A Collaborative Effort To Forecast Influenza Seasons In the United States," Epidemics, vol. 24, (2018), pp. 26-33.

Lu, Fred Sun et al. "Accurate Influenza Monitoring and Forecasting Using Novel Internet Data Streams: A Case Study In the Boston Metropolis," JMIR Public Health and Surveillance, (2018), vol. 4, Issue 1:e4, (18 pages). DOI:10.2196/publichealth.8950.

Paul, Susannah et al. "Modeling and Forecasting Influenza-Like Illness (ILI) In Houston, Texas Using Three Surveillance Data Capture Mechanisms," Online Journal of Public Health Informatics, vol. 9, No. 2:e187, (2017). doi:10.5210/ojphi.v9i2.8004. PMID: 29026453. PMCID: PMC5630275.

Sharma, Vikash Chandra et al. "Ensemble Approach For Zoonotic Disease Forecasting Using Machine Learning Techniques," International Journal of Business Analytics and Intelligence, vol. 3, Issue 2, Oct. 2015, pp. 11-24.

Song, Xin et al. "Time Series Analysis Of Influenza Incidence In Chinese Provinces From 2004 To 2011," Medicine (Baltimore), vol. 95, No. 26:e3929, Jun. 2016, pp. 1-7. doi: 10.1097/MD. 0000000000003929. PMID: 27367989. PMCID: PMC4937903.

Tran, Thien Q. et al. "Seasonal-Adjustment Based Feature Selection Method For Predicting Epidemic With Large-Scale Search Engine Logs," KDD '19: Proceedings of the 25th ACM SIGKDD International Conference on Knowledge Discovery & Data Mining, Jul. 2019, pp. 2857-2866. doi.10.1145/3292500.3330766.

* cited by examiner

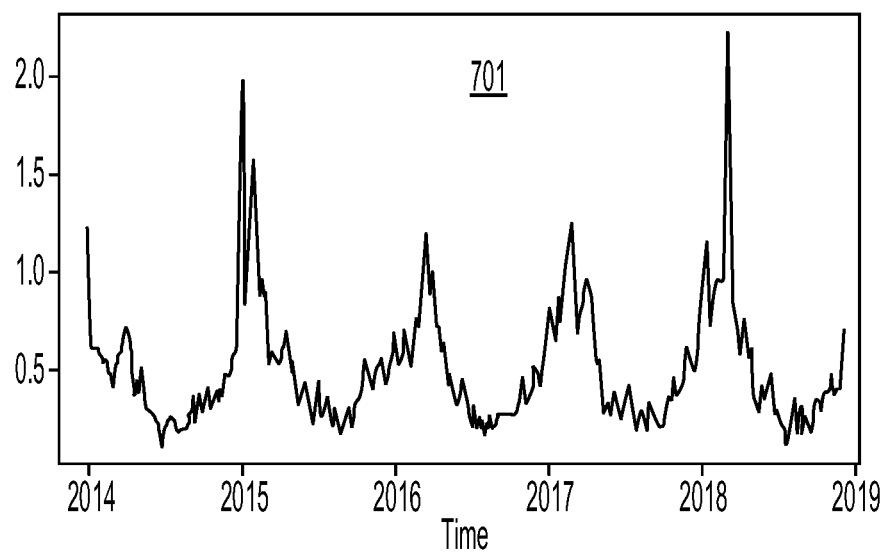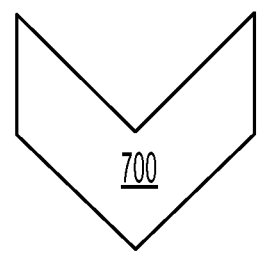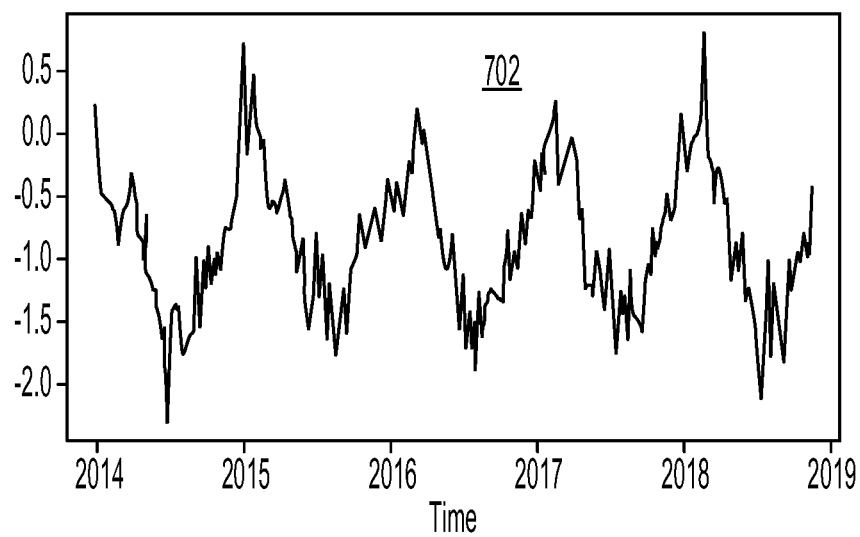
FIG. 7

```
                                                            404
```

```
┌─────────────────────────────────────────────────────────────┐
│                                                             │
│   Generate a trend component of the training input timeseries data object
│                              801                            │
│                                                             │
└─────────────────────────────────────────────────────────────┘
                              │
                              ▼
┌─────────────────────────────────────────────────────────────┐
│                                                             │
│ Generate a seasonality component of the training input timeseries data object
│                              802                            │
│                                                             │
└─────────────────────────────────────────────────────────────┘
                              │
                              ▼
┌─────────────────────────────────────────────────────────────┐
│                                                             │
│  Generate an erorr component of the training input timeseries data object
│                              803                            │
│                                                             │
└─────────────────────────────────────────────────────────────┘
                              │
                              ▼
┌─────────────────────────────────────────────────────────────┐
│                                                             │
│  Generate the seasonally-adjusted training input timeseries data object
│                              804                            │
│                                                             │
└─────────────────────────────────────────────────────────────┘
```

FIG. 8

SEASONALLY ADJUSTED PREDICTIVE DATA ANALYSIS

BACKGROUND

Various embodiments of the present invention address technical challenges related to performing seasonally adjusted predictive data analysis. Various embodiments of the present invention address the shortcomings of existing seasonally adjusted predictive data analysis systems and disclose various techniques for efficiently and reliably performing seasonally adjusted predictive data analysis operations.

BRIEF SUMMARY

In general, embodiments of the present invention provide methods, apparatus, systems, computing devices, computing entities, and/or the like for performing seasonally adjusted predictive data analysis. Certain embodiments of the present invention utilize systems, methods, and computer program products that perform seasonally adjusted predictive data analysis by utilizing trained autoregressive integrated moving average (ARIMA) models that perform seasonal adjustment operations both as part of the input preprocessing for the ARIMA models and as part of the differencing operations of the ARIMA models.

In accordance with one aspect, a method is provided. In one embodiment, the method comprises: identifying a seasonally-adjusted training input timeseries data object and a seasonally-adjusted testing timeseries data object; generating a trained autoregressive integrated moving average (ARIMA) model using the seasonally-adjusted training input timeseries data object, wherein generating the trained ARIMA model comprises: determining an optimal differencing order hyper-parameter of the trained ARIMA model that is configured to transform the seasonally-adjusted training input timeseries data object into a stationary seasonally-adjusted training input timeseries data object, determining an optimal lag order hyper-parameter of the trained ARIMA model and an optimal moving average order hyper-parameter of the trained ARIMA model that are collectively configured to optimize a model utility measure for the trained ARIMA model, and determining one or more optimal parameters of the trained ARIMA model that are configured to enable the trained ARIMA model to describe the seasonally-adjusted training input timeseries data object given the optimal differencing degree hyper-parameter, the optimal lag order hyper-parameter, and the optimal moving average order hyper-parameter; determining a validation determination for the trained ARIMA model based at least in part on the seasonally-adjusted testing timeseries data object; determining whether the validation determination describes a positive validation; and in response to determining that the validation determination describes the positive validation, enabling performance of a predictive inference using the trained ARIMA model in order to generate one or more prospective time-lagged predictions and to perform one or more prediction-based actions based at least in part on the one or more prospective time-lagged predictions.

In accordance with another aspect, a computer program product is provided. The computer program product may comprise at least one computer-readable storage medium having computer-readable program code portions stored therein, the computer-readable program code portions comprising executable portions configured to: identify a seasonally-adjusted training input timeseries data object and a seasonally-adjusted testing timeseries data object; generate a trained autoregressive integrated moving average (ARIMA) model using the seasonally-adjusted training input timeseries data object, wherein generating the trained ARIMA model comprises: determining an optimal differencing order hyper-parameter of the trained ARIMA model that is configured to transform the seasonally-adjusted training input timeseries data object into a stationary seasonally-adjusted training input timeseries data object, determining an optimal lag order hyper-parameter of the trained ARIMA model and an optimal moving average order hyper-parameter of the trained ARIMA model that are collectively configured to optimize a model utility measure for the trained ARIMA model, and determining one or more optimal parameters of the trained ARIMA model that are configured to enable the trained ARIMA model to describe the seasonally-adjusted training input timeseries data object given the optimal differencing degree hyper-parameter, the optimal lag order hyper-parameter, and the optimal moving average order hyper-parameter; determine a validation determination for the trained ARIMA model based at least in part on the seasonally-adjusted testing timeseries data object; determine whether the validation determination describes a positive validation; and in response to determining that the validation determination describes the positive validation, enable performance of a predictive inference using the trained ARIMA model in order to generate one or more prospective time-lagged predictions and to perform one or more prediction-based actions based at least in part on the one or more prospective time-lagged predictions.

In accordance with yet another aspect, an apparatus comprising at least one processor and at least one memory including computer program code is provided. In one embodiment, the at least one memory and the computer program code may be configured to, with the processor, cause the apparatus to: identify a seasonally-adjusted training input timeseries data object and a seasonally-adjusted testing timeseries data object; generate a trained autoregressive integrated moving average (ARIMA) model using the seasonally-adjusted training input timeseries data object, wherein generating the trained ARIMA model comprises: determining an optimal differencing order hyper-parameter of the trained ARIMA model that is configured to transform the seasonally-adjusted training input timeseries data object into a stationary seasonally-adjusted training input time-series data object, determining an optimal lag order hyper-parameter of the trained ARIMA model and an optimal moving average order hyper-parameter of the trained ARIMA model that are collectively configured to optimize a model utility measure for the trained ARIMA model, and determining one or more optimal parameters of the trained ARIMA model that are configured to enable the trained ARIMA model to describe the seasonally-adjusted training input timeseries data object given the optimal differencing degree hyper-parameter, the optimal lag order hyper-parameter, and the optimal moving average order hyper-parameter; determine a validation determination for the trained ARIMA model based at least in part on the seasonally-adjusted testing timeseries data object; determine whether the validation determination describes a positive validation; and in response to determining that the validation determination describes the positive validation, enable performance of a predictive inference using the trained ARIMA model in order to generate one or more prospective time-lagged predictions and to perform one or more prediction-based actions based at least in part on the one or more prospective time-lagged predictions.

BRIEF DESCRIPTION OF THE DRAWINGS

Figure 1:
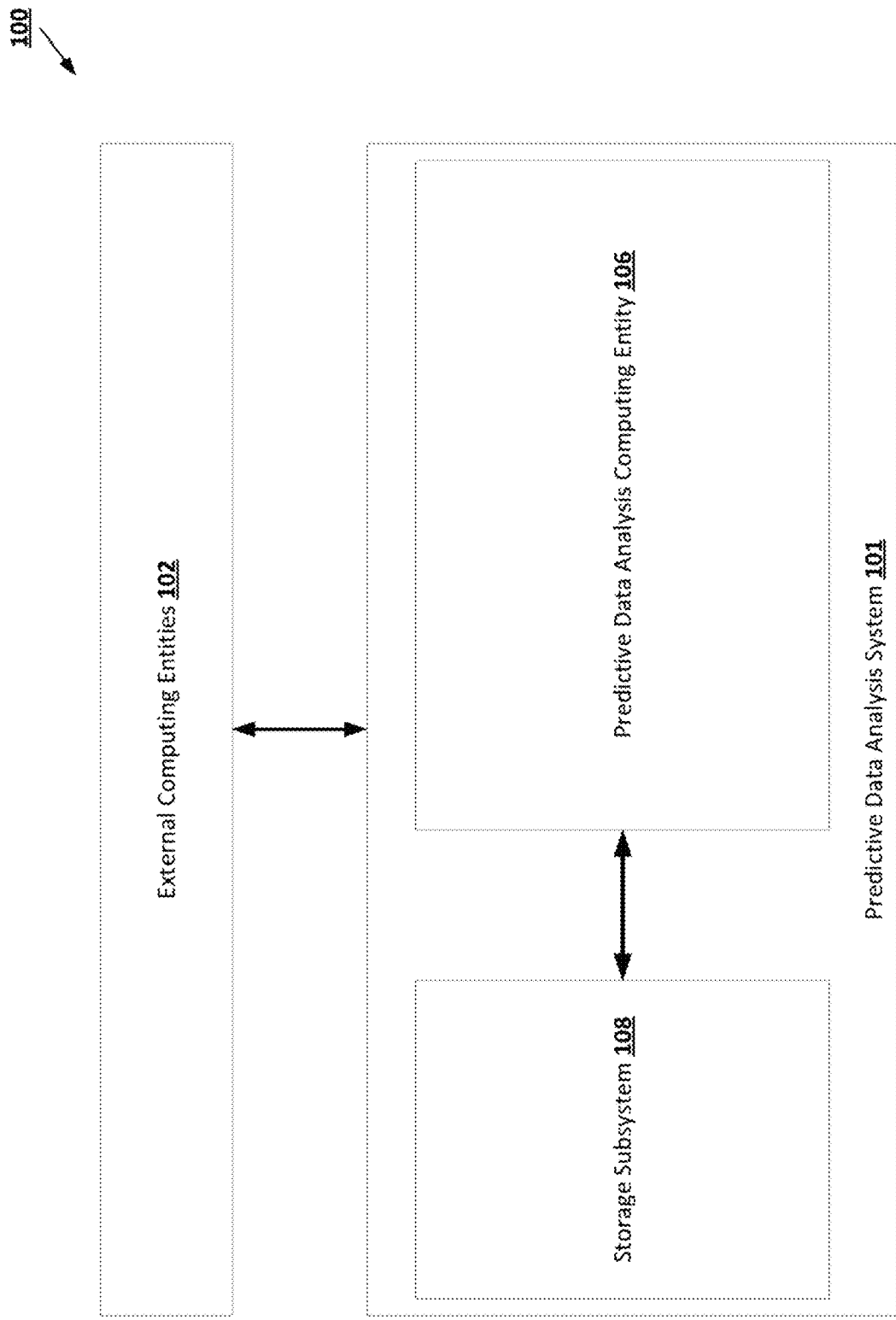

Having thus described the invention in general terms, reference will now be made to the accompanying drawings, which are not necessarily drawn to scale, and wherein:

FIG. 1 provides an exemplary overview of an architecture that can be used to practice embodiments of the present invention.

Figure 2:
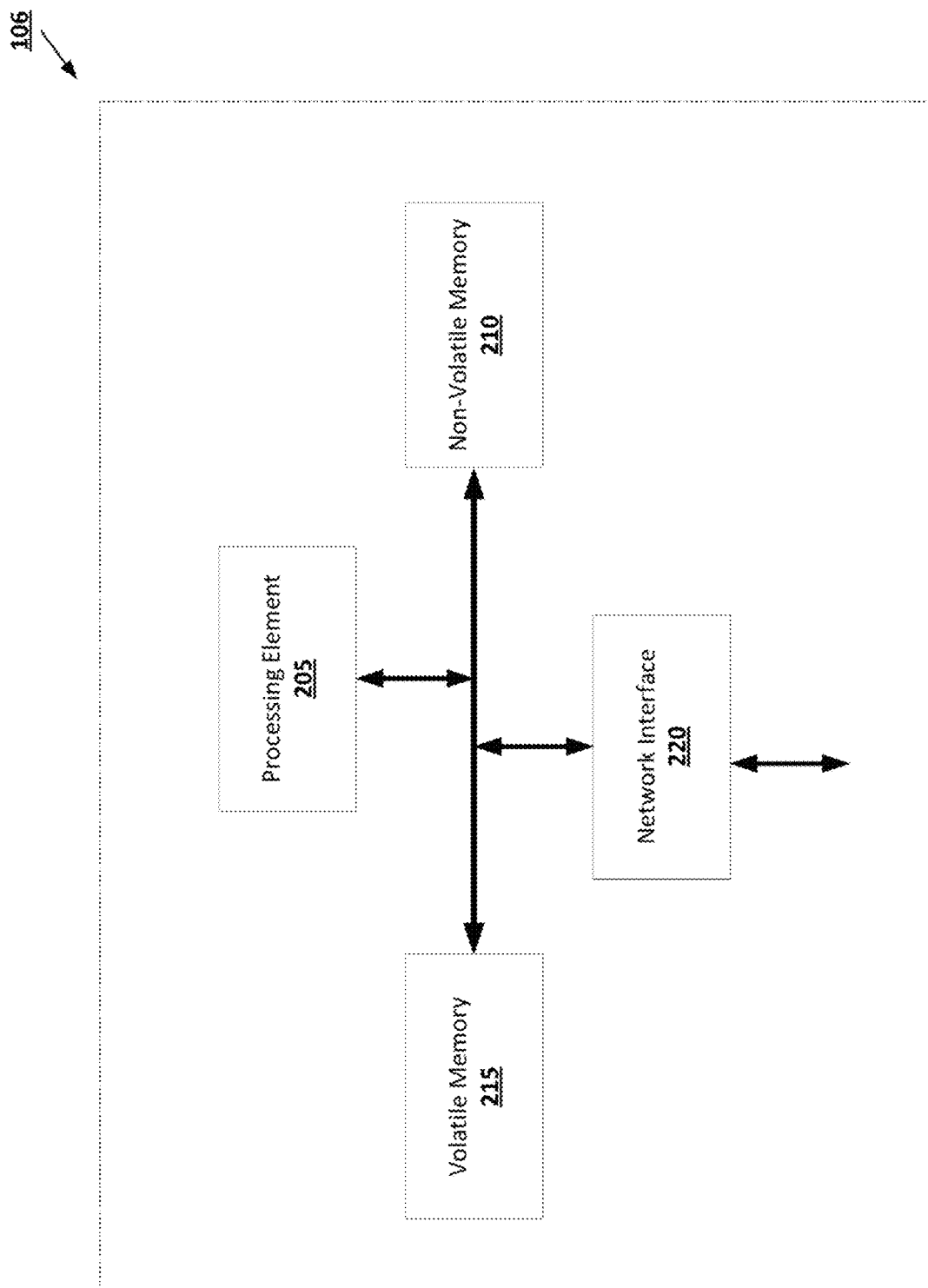

FIG. 2 provides an example predictive data analysis computing entity in accordance with some embodiments discussed herein.

Figure 3:
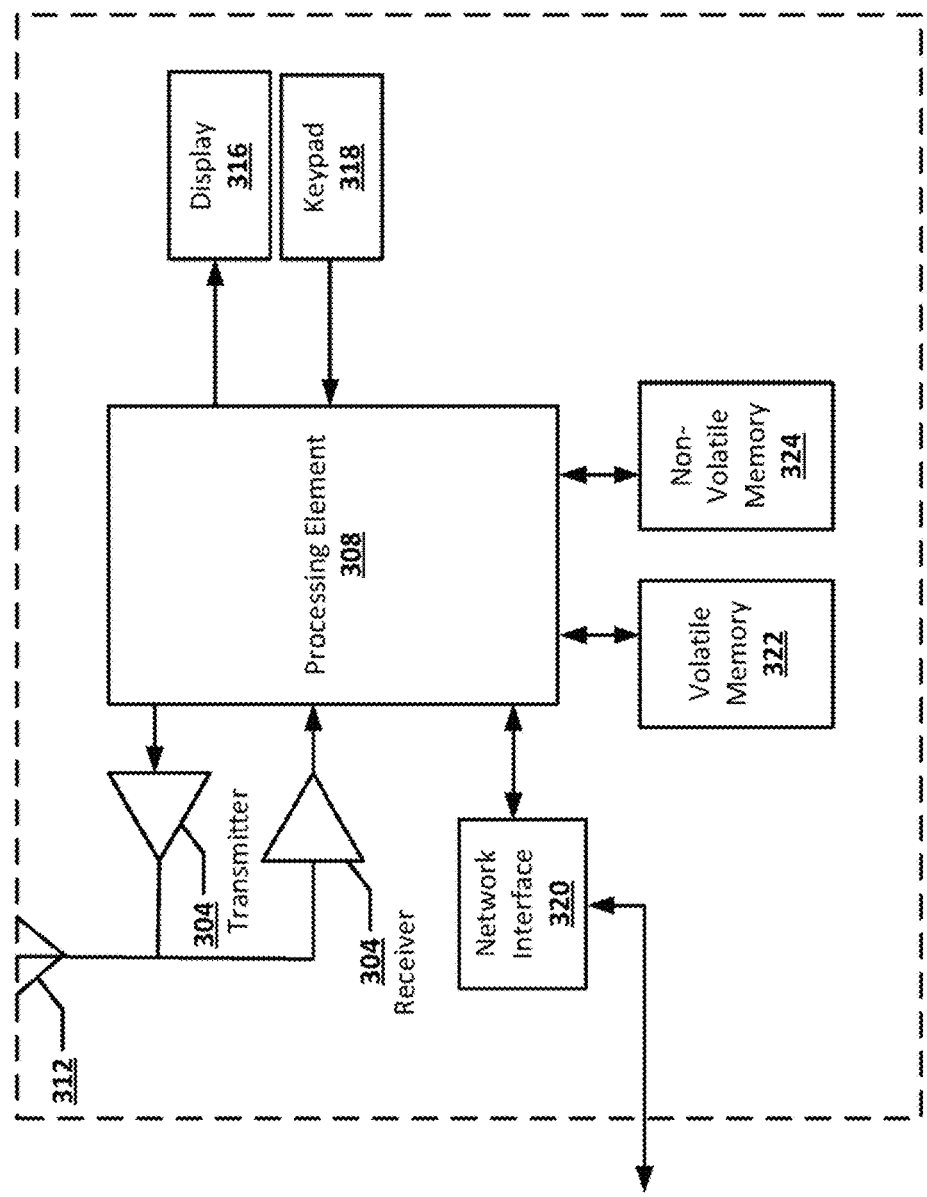

FIG. 3 provides an example external computing entity in accordance with some embodiments discussed herein.

Figure 4:
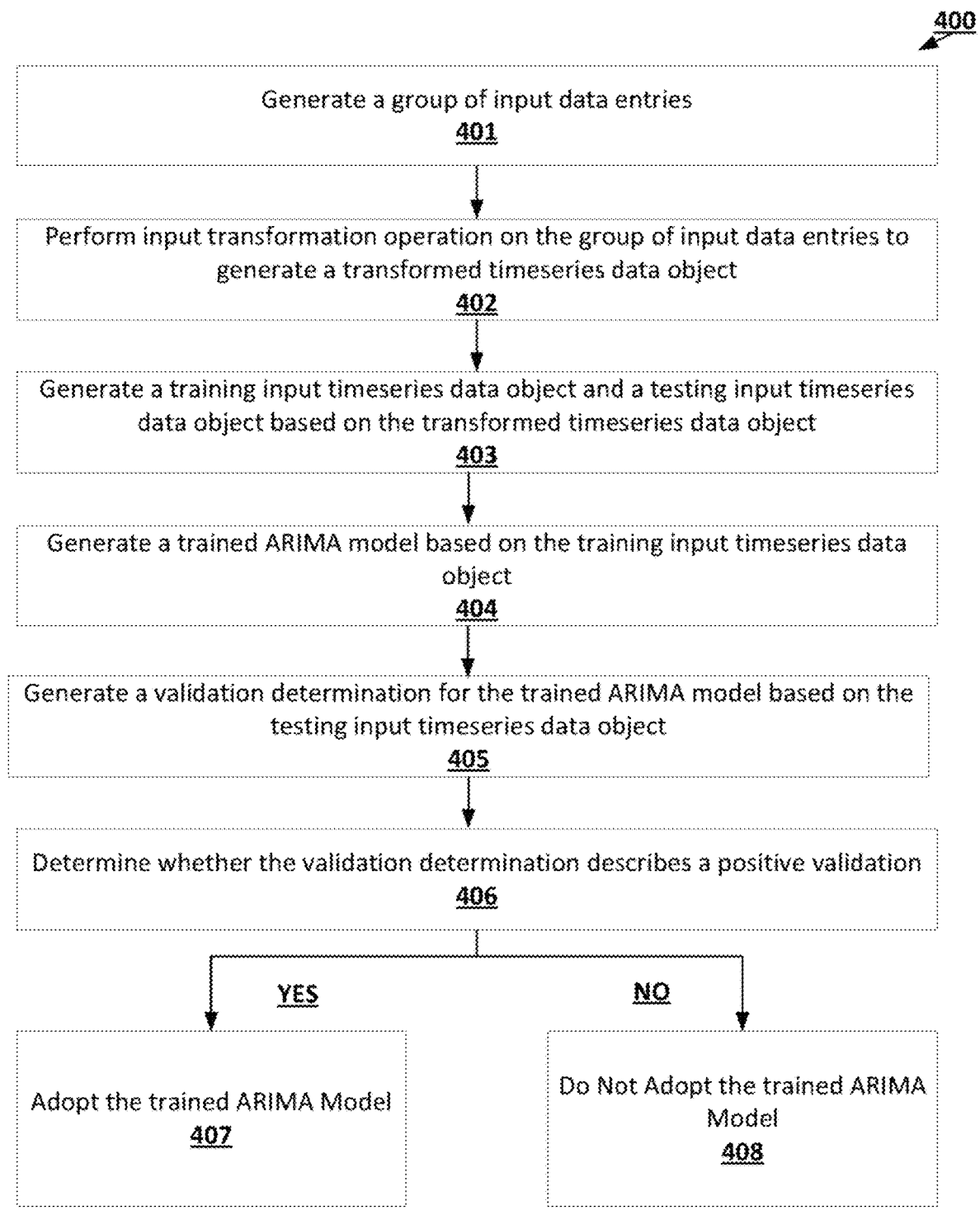

FIG. 4 is a flowchart diagram of an example process for training an ARIMA model to perform seasonally-adjusted predictive data analysis operations in accordance with some embodiments discussed herein.

Figure 5:
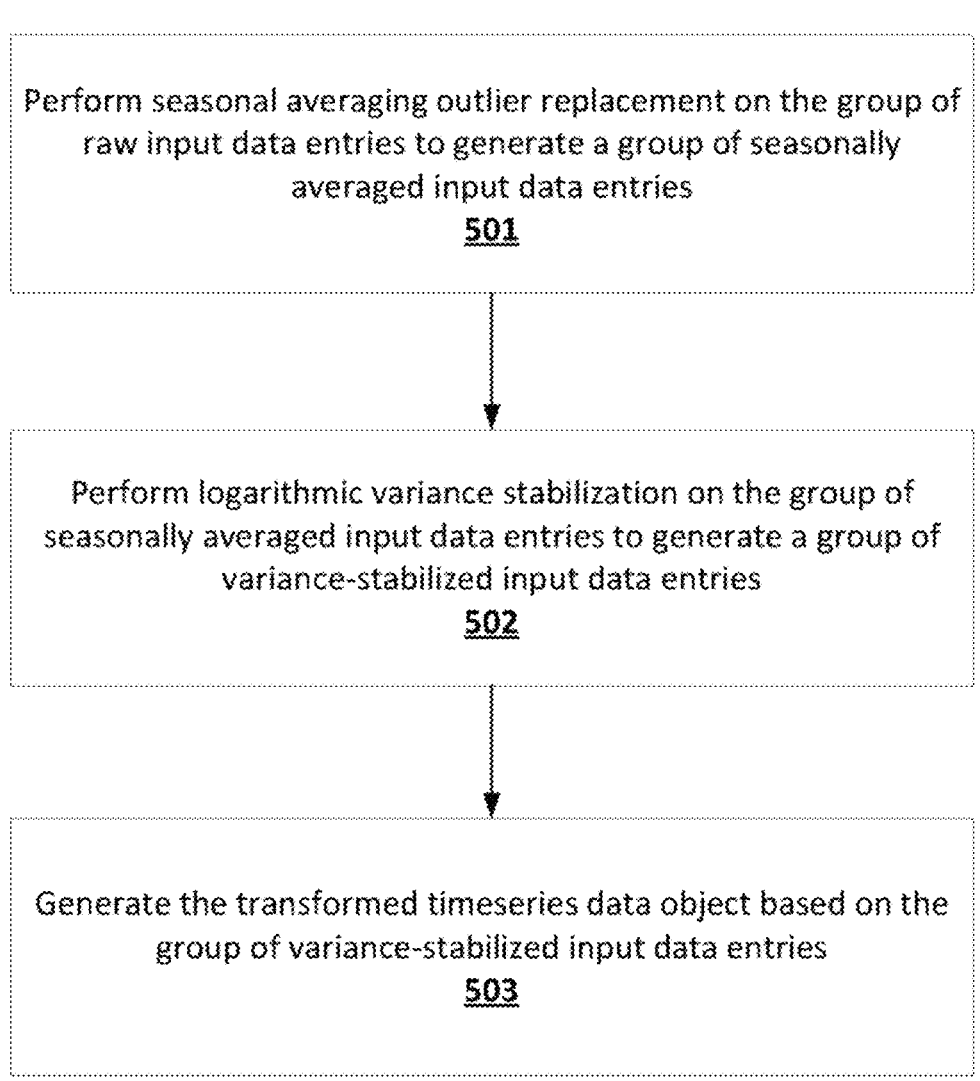

FIG. 5 is a flowchart diagram of an example process for performing input transformation operations on a group of raw input data entries in accordance with some embodiments discussed herein.

Figure 6:
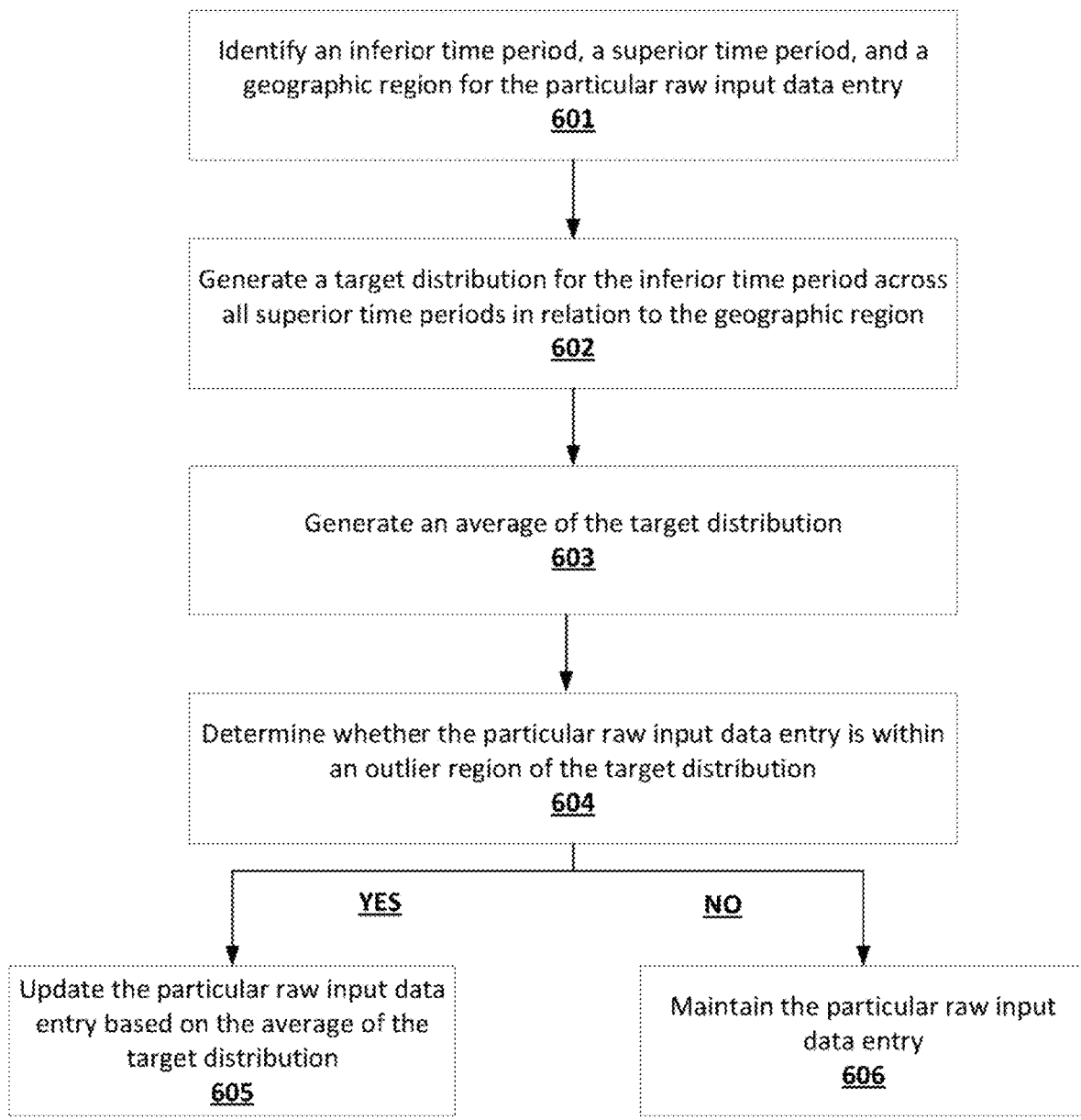

FIG. 6 is a flowchart diagram of an example process for performing seasonal averaging outlier replacement on a group of raw input data entries in accordance with some embodiments discussed herein.

FIG. 7 provides an operational example of a logarithmic variance stabilization operation in accordance with some embodiments discussed herein.

FIG. 8 is a flowchart diagram of an example process for generating a seasonally adjusted training input timeseries data object in accordance with some embodiments discussed herein.

Figure 9:
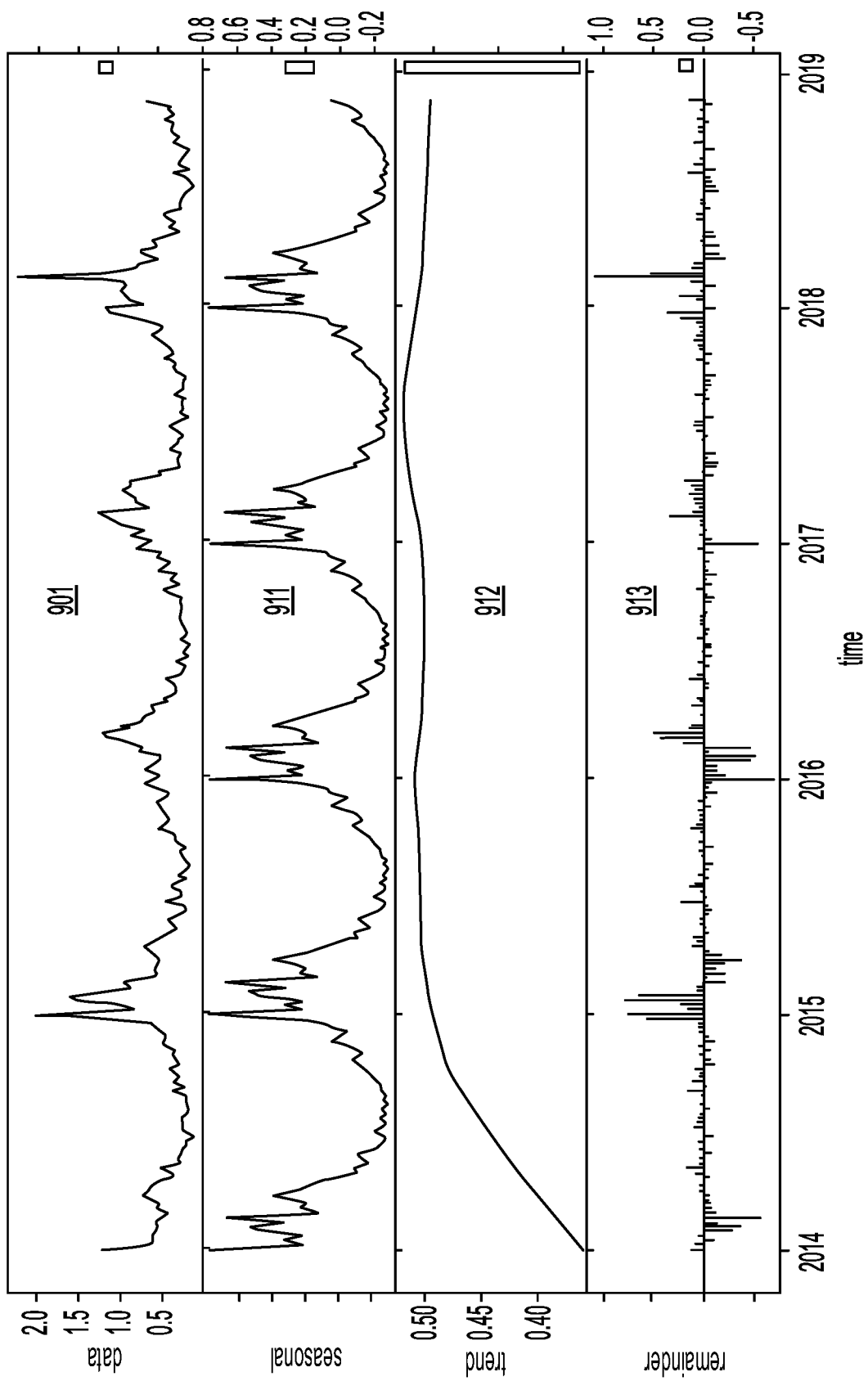

FIG. 9 provides an operational example of generating a trend component, a seasonality component, and an error component of a training input timeseries data object in accordance with some embodiments discussed herein.

Figure 10:
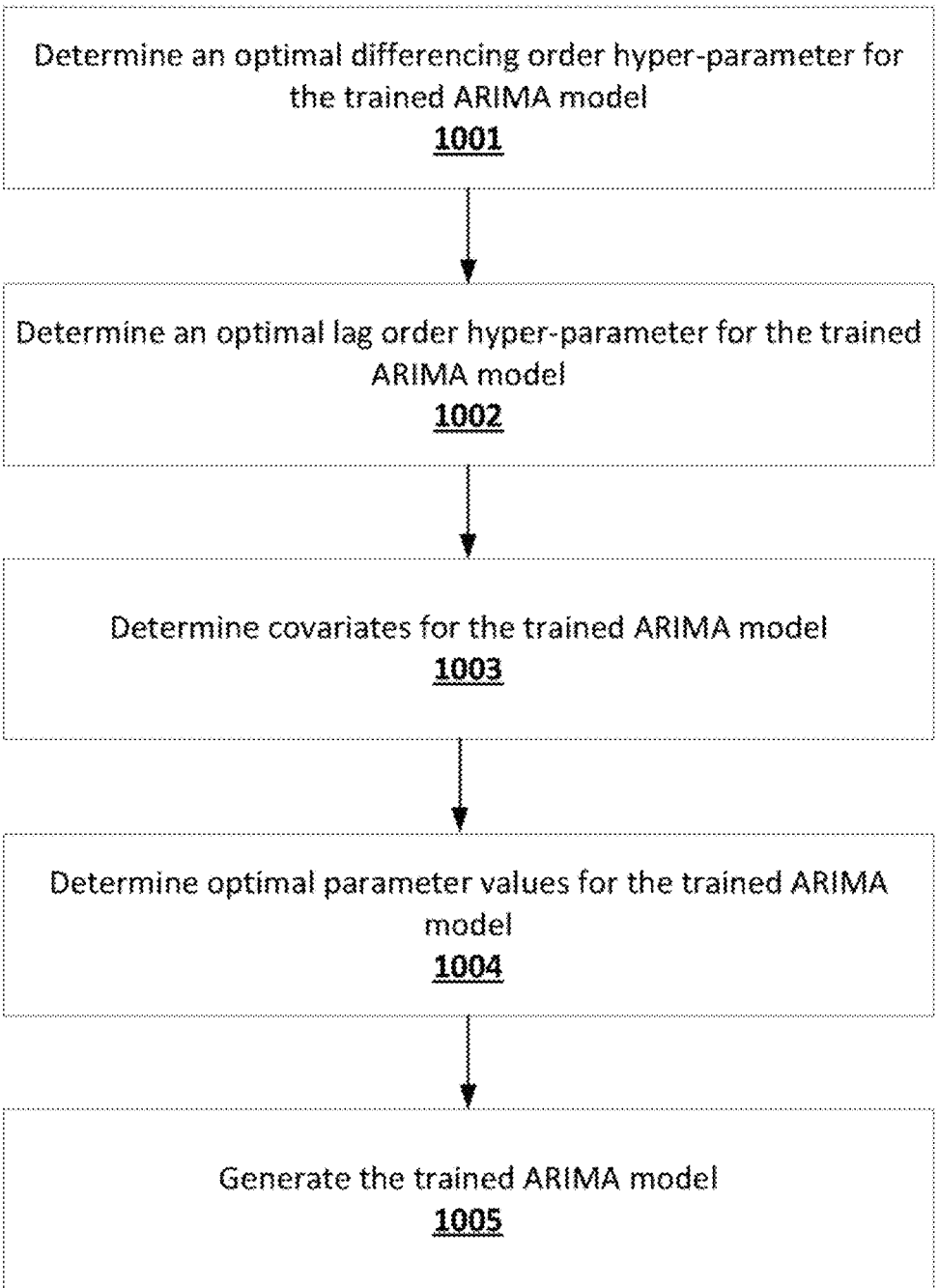

FIG. 10 is a flowchart diagram of an example process for training an ARIMA model using a seasonally adjusted training input timeseries data object in accordance with some embodiments discussed herein.

Figure 11:
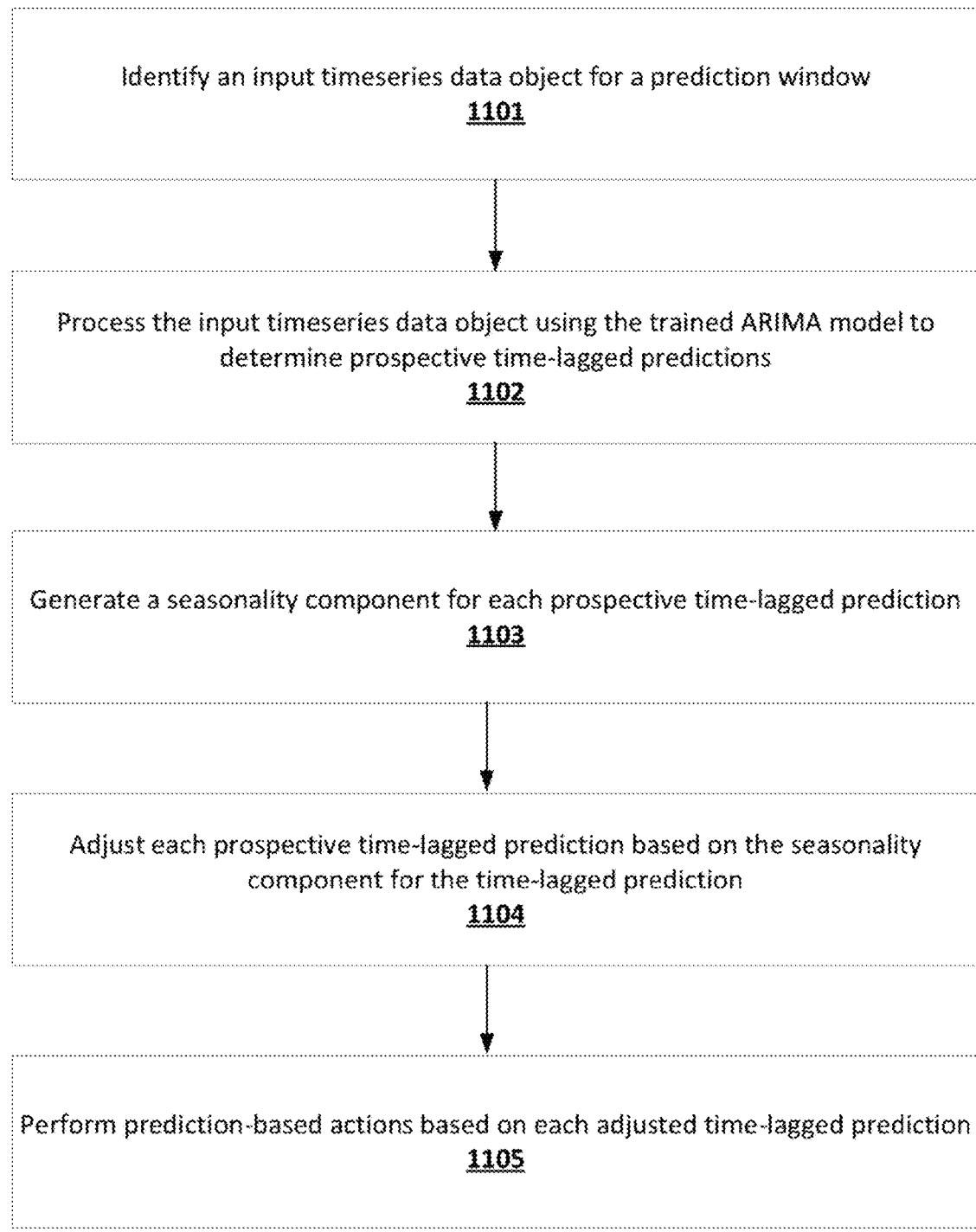

FIG. 11 is a flowchart diagram of an example process for performing a predictive inference using a trained AMNIA model in accordance with some embodiments discussed herein.

Figure 12:
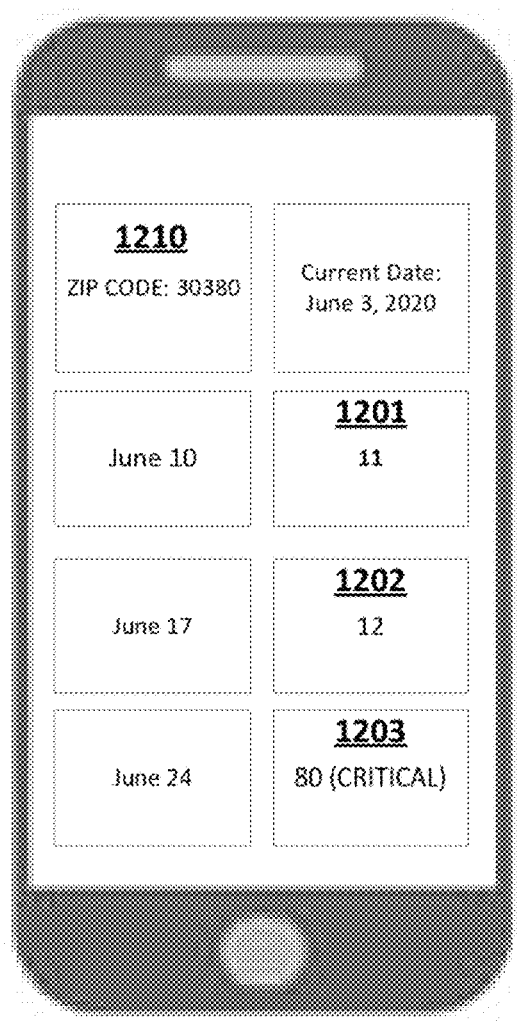

FIG. 12 provides an operational example of a prediction output user interface in accordance with some embodiments discussed herein.

DETAILED DESCRIPTION

Various embodiments of the present invention now will be described more fully hereinafter with reference to the accompanying drawings, in which some, but not all, embodiments of the inventions are shown. Indeed, these inventions may be embodied in many different forms and should not be construed as limited to the embodiments set forth herein; rather, these embodiments are provided so that this disclosure will satisfy applicable legal requirements. The term "or" is used herein in both the alternative and conjunctive sense, unless otherwise indicated. The terms "illustrative" and "exemplary" are used to be examples with no indication of quality level. Like numbers refer to like elements throughout. Moreover, while certain embodiments of the present invention are described with reference to predictive data analysis, one of ordinary skill in the art will recognize that the disclosed concepts can be used to perform other types of data analysis.

I. Overview

Various embodiments of the present invention disclose innovative and technologically advantageous techniques for more efficiently training ARIMA models in order to utilize those models to perform seasonally-adjusted predictive data analysis tasks. ARIMA models provide powerful tools for modeling timeseries data even when such timeseries data is non-stationary. To reduce the stationarity of input data, ARIMA models perform a number of differencing operations to create new timeseries data with more stable variances over time. The number of differencing operations of an ARIMA model is determined based on a differencing order hyper-parameter of an ARIMA model during training. This means that, during training of an ARIMA model, various computationally resource intensive differencing operations should be performed to determine an optimal number of difference operations for a given timeseries dataset. This in turn means that, for more complex data with higher levels of non-stationarity, the training of ARIMA models could be computationally resource intensive.

Various embodiments of the present invention enable techniques for training ARIMA models that reduce the need for the noted computationally resource-intensive differencing operations during training of the ARIMA models. For example, in some embodiments, the training input data for training an ARIMA model is first preprocessed using outlier replacement techniques and/or variance stabilization techniques configured to reduce cross-temporal variance change of such training input data. As a result, before training of the ARIMA model, the input training data can be transformed using relatively less resource-intensive operations (e.g., outlier replacement using seasonal averaging, variance stabilization using logarithmic transformations, and/or the like) in order to reduce the number of differencing operations that need to be performed during training of the noted ARIMA models. This in turn means that, by utilizing various techniques disclosed throughout the present document, many ARIMA models would be easier and more efficient to train, which increases accessibility and reliability of the noted ARIMA models.

Accordingly, by improving efficiency of training ARIMA models, various embodiments of the present invention improve the overall efficiency of predictive data analysis frameworks that utilize such models. Moreover, improving efficiency of training ARIMA models makes retraining of those models using newly-arriving data more cost-effective, which in turn means that trained ARIMA models will be more up to date and trained using larger repositories of training data. Thus, the collective effect of many of the noted technological advantages offered by various embodiments of the present invention is an increase in efficiency, accuracy, and reliability of various existing predictive data analysis systems, especially predictive data analysis systems configured to perform timeseries-based predictive inferences using data with high degrees of seasonality (e.g., influenza outbreak prediction systems).

II. Definitions

The term "raw input data entry" may refer to a data construct that describes a monitored state of an observed phenomenon over a corresponding unit of time, where the observed phenomenon may be associated with a particular geographic region. Collectively, a group of raw input data entries may describe the monitored state of two or more observed phenomena over many periods of times, where each of the two or more observed phenomena may relate to a geographic region of a group of a geographic regions, and where the group of geographic regions may include at least two geographic regions that are overlapping (e.g., a geographic region of New York City metropolitan area and a geographic region of the state of New York). In some embodiments, a raw input data entry describes an estimated percentage of flu patients in a corresponding geographic region during a corresponding week. In some of the noted embodiments, the group of raw input data entries may describe estimated percentages of flu patients across many geographic regions (which may include overlapping geographic regions) during a group of weeks in a historical monitored period (e.g., a historical monitored period between 2014 and 2019).

The term "inferior time period" may refer to a data construct that describes a time period that is deemed to be a subcomponent of a superior time period in a manner that the temporal position of the inferior time period within the superior time period describes an expected pattern of seasonality for the overall timeseries data so that significant deviations between common inferior time periods across different superior time periods may be deemed less statistically significant. Examples of inferior time periods may include weeks, months, or seasons, while examples of superior time periods may include years. In an exemplary embodiment, a year may be expected to display seasonality patterns that in turn causes particular weeks of the year to show an expected level of consistency across years, an assumption that in turn causes significant deviations from cross-annual distributions for the raw input data entry of a particular week to be deemed less statistically significant and thus replaceable (e.g., if the raw input data entry for week n differs significantly from the average value for week n across all years in a monitored period, the raw input data entry for week n may be deemed less statistically significant and thus replaceable).

The term "superior time period" may refer to a data construct that describes a time period that is deemed to include two or more inferior time periods characterized by a temporal ordering that assigns a temporal position to each of the noted inferior time periods, where the temporal ordering describes an expected pattern of seasonality for the overall timeseries data in a manner that makes significant deviations between common inferior time periods across different superior time periods be deemed less statistically significant. As noted above, an example of a superior time period may describe a year, which may include various inferior time periods (e.g., 4 seasons, 12 months, 52 weeks, 2 half-years, and/or the like), where the temporal position of each inferior time period is expected to prescribe an expected level of consistency for the raw input data entry values for the inferior time period across multiple years, an assumption that in turn causes significant deviations from cross-annual distributions for the raw input data entry of a particular inferior time period to be deemed less statistically significant and thus replaceable.

The term "trend component" may refer to a data construct that describes long-term increases or decreases in a timeseries data object across the totality of the time window associated with the timeseries data object. In some embodiments, to generate the trend component of a timeseries data object, a predictive data analysis computing entity performs a smoothing operation on the timeseries data object in a manner configured to represent buckets of timeseries data object values by a single representative value. For example, in some embodiments, to perform the noted smoothing operation, the predictive data analysis computing entity may apply local weighted regression on the timeseries data object. An example bucket size for a smoothing operation that can be performed as part of a trend generation process is a bucket size that describes 52 contiguous data entries of the noted timeseries data object.

The term "seasonality component" may refer to a data construct that describes short-term fluctuations of a timeseries data object across portions of the timeseries data object that relate to particular superior time periods (e.g., particular years). In some embodiments, given a timeseries data object that includes x inferior time periods (e.g., 52 weeks) of L superior time periods (e.g., ten years), the seasonality of the training input timeseries data object is determined by determining, for each of the x inferior time periods, a seasonality value based at least in part on a measure of statistical distribution (e.g., an average) of the timeseries data object values for the inferior time period across all of the L superior time periods (e.g., by calculating $[i+(i+x)+(i+2x)+ \ldots +(i+Lx)]/L$, where i describes the particular inferior time period of a first superior time period in the monitoring window, such as a particular week of a first year of the monitoring window).

The term "error component" may refer to a data construct that describes the residual value generated after subtracting the trend component of a timeseries data object and the seasonality component of the timeseries data object from the noted timeseries data object. Accordingly, the error component of a timeseries data object may describe variations in the timeseries data object not captured by either the long-term movements of the timeseries data object as represented by the trend component of the timeseries data object, or the short-term fluctuations of the timeseries data object as represented by the error component of the timeseries data object.

A "hyper-parameter" of an ARIMA model may refer to a data construct that describes an aspect of the number of autoregressive operations of the ARIMA model, the number of differencing operations of the ARIMA model, the number of lagged forecast error adjustment operations of the ARIMA model, or the number of covariate terms of an ARIMA model. In particular, if the ARIMA model is a non-seasonal ARIMA model, the hyper-parameters of the ARMIA model may include: (i)p, which describes the number of autoregressive terms of the ARMIA model and is also known as the lag order hyper-parameter of the ARIMA model; (ii) d, which describes the number of non-seasonal differencing operations performed to make the data stationary, and is also known as the differencing order hyper-parameter of the ARIMA mode; and (iii) q, which describes the number of lagged forecast error adjustment operations of the ARIMA model, and is also known as the moving average order of the ARIMA model. Moreover, if the ARIMA model is a seasonal ARIMA model, the hyper-parameters of the ARIMA model may include: (i) p, which describes the number of autoregressive terms of the ARIMA model and is also known as the lag order hyper-parameter of the ARIMA model; (ii) d, which describes the number of non-seasonal differencing operations performed to make the data stationary, and is also known as the differencing order hyper-parameter of the ARIMA mode; (iii) q, which describes the number of lagged forecast error adjustment operations of the ARIMA model, and is also known as the moving average order of the ARIMA model; (iv) P, which describes the number of seasonal autoregressive terms of the ARIMA model and is also known as the seasonal lag order hyper-parameter of the ARIMA model; (v) D, which describes the number of seasonal differencing operations performed to make the data stationary, and is also known as the seasonal differencing order hyper-parameter of the ARIMA mode; and (vi) Q, which describes the number of seasonal lagged forecast error adjustment operations of the ARIMA model, and is also known as the seasonal moving average order of the ARIMA model. In some embodiments, hyper-parameters of an ARIMA model may optionally include the number of covariate terms of the ARIMA model.

A "covariate" of an ARIMA model may refer to a data construct that describes a value supplied as part of a linear term of the ARIMA model, where the noted value is configured to describe an observed/forecasted state of a target phenomenon during a time period that occurs subsequent to a time period associated with a current iteration of the ARIMA model. For example, consider an ARIMA model that has a first covariate describing a one-week-lagged prospective flu patient percentage, a second covariate describing a two-week-lagged prospective flu patient percentage, and a third covariate describing a three-week-lagged prospective flu patient percentage. In the noted example, during a testing iteration of the noted ARIMA model that is associated with week 20 of 2018, the values of the three covariates may be determined based at least in part on historical data about flu patient percentages of weeks 21-23 of 2018 respectively; however, during a prediction iteration of the noted ARIMA model that is associated with week 20 of 2021, the values of three covariates may be estimated based at least in part on trained parameters of the model and may at least a part of the predictive output of running the trained ARIMA model on a predictive inference iteration associated with week 20 of 2018. Thus, according to the latter scenario (i.e., the prediction iteration), the values of the covariates may be used to determine prospective time-lagged predictions that may be outputs of a trained ARIMA model.

A "parameter" of an ARIMA model may refer to a data construct that describes any value that is determined during training of the ARIMA model but is not a hyper-parameter of the ARIMA model. For example, parameters of the ARIMA model may include coefficients applied to hyper-parameters of the ARIMA model and/or applied to covariates of the ARIMA model as part of the linear operations of the ARIMA model. In some embodiments, training of an ARIMA model includes determining optimal values for parameters of the ARIMA model subsequent to determining optimal values for hyper-parameters of the ARIMA model.

The "model utility measure" may refer to a data construct that describes at least one of a measure of fitness of the forecast of an ARIMA model relative to ground-truth data and a simplicity (e.g., the number of parameters, the number of terms, and/or the like) of the ARIMA model. In some embodiments, a model utility measure for an ARIMA model may be determined based on at least one of the following: an Akaike information criterion measure (AIC) for the ARIMA model, a corrected Akaike information criterion measure (AICc) for the ARIMA model, and a Bayesian information criterion measure (BIC) for the ARIMA model. The AIC for an ARIMA model may be determined in accordance with the equation $AIC=-2\log(L)+2(p+q+k)$, where L is the maximum likelihood estimation of the forecast data generated by the ARIMA model and k describes existence of the intercept of the ARIMA model (such that, if k=1, then there is an intercept for the ARIMA model, and if k=0, then there is no intercept for the ARIMA model). The AICc for an ARIMA model may be determined in accordance with the equation $AICc=AIC+(2(p+q+k)(p+q+k+1))/(T-p-q-k-1)$, and the BIC for an ARIMA model may be determined in accordance with the equation $BIC=AIC+(\log(T)-2)(p+q+k)$, where T describes the number of observations used for estimation (i.e., for determining AIC/BIC). In some embodiments, if two or more ARIMA models have different differencing order hyper-parameters, their model utility measures can be determined using one or more structure-agnostic error measures for the noted models, such as using at least one of root mean squared errors (RMSEs) for the noted models, mean absolute percentage errors (MAPE5) for the noted models, mean absolute errors (MAEs) for the noted models, mean percentage errors (MPEs) for the noted models, and/or the like.

III. Computer Program Products, Methods, and Computing Entities

Embodiments of the present invention may be implemented in various ways, including as computer program products that comprise articles of manufacture. Such computer program products may include one or more software components including, for example, software objects, methods, data structures, or the like. A software component may be coded in any of a variety of programming languages. An illustrative programming language may be a lower-level programming language such as an assembly language associated with a particular hardware architecture and/or operating system platform. A software component comprising assembly language instructions may require conversion into executable machine code by an assembler prior to execution by the hardware architecture and/or platform. Another example programming language may be a higher-level programming language that may be portable across multiple architectures. A software component comprising higher-level programming language instructions may require conversion to an intermediate representation by an interpreter or a compiler prior to execution.

Other examples of programming languages include, but are not limited to, a macro language, a shell or command language, a job control language, a script language, a database query or search language, and/or a report writing language. In one or more example embodiments, a software component comprising instructions in one of the foregoing examples of programming languages may be executed directly by an operating system or other software component without having to be first transformed into another form. A software component may be stored as a file or other data storage construct. Software components of a similar type or functionally related may be stored together such as, for example, in a particular directory, folder, or library. Software components may be static (e.g., pre-established or fixed) or dynamic (e.g., created or modified at the time of execution).

A computer program product may include a non-transitory computer-readable storage medium storing applications, programs, program modules, scripts, source code, program code, object code, byte code, compiled code, interpreted code, machine code, executable instructions, and/or the like (also referred to herein as executable instructions, instructions for execution, computer program products, program code, and/or similar terms used herein interchangeably). Such non-transitory computer-readable storage media include all computer-readable media (including volatile and non-volatile media).

In one embodiment, a non-volatile computer-readable storage medium may include a floppy disk, flexible disk, hard disk, solid-state storage (SSS) (e.g., a solid state drive (SSD), solid state card (SSC), solid state module (SSM), enterprise flash drive, magnetic tape, or any other non-transitory magnetic medium, and/or the like. A non-volatile computer-readable storage medium may also include a punch card, paper tape, optical mark sheet (or any other physical medium with patterns of holes or other optically recognizable indicia), compact disc read only memory (CD-ROM), compact disc-rewritable (CD-RW), digital versatile disc (DVD), Blu-ray disc (BD), any other non-transitory optical medium, and/or the like. Such a non-volatile computer-readable storage medium may also include read-only memory (ROM), programmable read-only memory (PROM), erasable programmable read-only memory (EPROM), electrically erasable programmable read-only memory (EEPROM), flash memory (e.g., Serial, NAND, NOR, and/or the like), multimedia memory cards (MMC), secure digital (SD) memory cards, SmartMedia cards, CompactFlash (CF) cards, Memory Sticks, and/or the like. Further, a non-volatile computer-readable storage medium may also include conductive-bridging random access memory (CBRAM), phase-change random access memory (PRAM), ferroelectric random-access memory (FeRAM), non-volatile random-access memory (NVRAM), magnetoresistive random-access memory (MRAM), resistive random-access memory (RRAM), Silicon-Oxide-Nitride-Oxide-Silicon memory (SONOS), floating junction gate random access memory (FJG RAM), Millipede memory, racetrack memory, and/or the like.

In one embodiment, a volatile computer-readable storage medium may include random access memory (RAM), dynamic random access memory (DRAM), static random access memory (SRAM), fast page mode dynamic random access memory (FPM DRAM), extended data-out dynamic random access memory (EDO DRAM), synchronous dynamic random access memory (SDRAM), double data rate synchronous dynamic random access memory (DDR SDRAM), double data rate type two synchronous dynamic random access memory (DDR2 SDRAM), double data rate type three synchronous dynamic random access memory (DDR3 SDRAM), Rambus dynamic random access memory (RDRAM), Twin Transistor RAM (TTRAM), Thyristor RAM (T-RAM), Zero-capacitor (Z-RAM), Rambus in-line memory module (RIMM), dual in-line memory module (DIMM), single in-line memory module (SIMM), video random access memory (VRAM), cache memory (including various levels), flash memory, register memory, and/or the like. It will be appreciated that where embodiments are described to use a computer-readable storage medium, other types of computer-readable storage media may be substituted for or used in addition to the computer-readable storage media described above.

As should be appreciated, various embodiments of the present invention may also be implemented as methods, apparatus, systems, computing devices, computing entities, and/or the like. As such, embodiments of the present invention may take the form of an apparatus, system, computing device, computing entity, and/or the like executing instructions stored on a computer-readable storage medium to perform certain steps or operations. Thus, embodiments of the present invention may also take the form of an entirely hardware embodiment, an entirely computer program product embodiment, and/or an embodiment that comprises combination of computer program products and hardware performing certain steps or operations. Embodiments of the present invention are described below with reference to block diagrams and flowchart illustrations. Thus, it should be understood that each block of the block diagrams and flowchart illustrations may be implemented in the form of a computer program product, an entirely hardware embodiment, a combination of hardware and computer program products, and/or apparatus, systems, computing devices, computing entities, and/or the like carrying out instructions, operations, steps, and similar words used interchangeably (e.g., the executable instructions, instructions for execution, program code, and/or the like) on a computer-readable storage medium for execution. For example, retrieval, loading, and execution of code may be performed sequentially such that one instruction is retrieved, loaded, and executed at a time. In some exemplary embodiments, retrieval, loading, and/or execution may be performed in parallel such that multiple instructions are retrieved, loaded, and/or executed together. Thus, such embodiments can produce specifically-configured machines performing the steps or operations specified in the block diagrams and flowchart illustrations. Accordingly, the block diagrams and flowchart illustrations support various combinations of embodiments for performing the specified instructions, operations, or steps.

IV. Exemplary System Architecture

FIG. 1 is a schematic diagram of an example architecture 100 for performing predictive data analysis. The architecture 100 includes a predictive data analysis system 101 configured to receive predictive data analysis requests from external computing entities 102, process the predictive data analysis requests to generate predictions, provide the generated predictions to the external computing entities 102, and automatically perform prediction-based actions based at least in part on the generated predictions. An example of a prediction that can be generated using the predictive data analysis system 101 is a prediction about likely future spread of an infectious disease like influenza.

In some embodiments, predictive data analysis system 101 may communicate with at least one of the external computing entities 102 using one or more communication networks. Examples of communication networks include any wired or wireless communication network including, for example, a wired or wireless local area network (LAN), personal area network (PAN), metropolitan area network (MAN), wide area network (WAN), or the like, as well as any hardware, software and/or firmware required to implement it (such as, e.g., network routers, and/or the like).

The predictive data analysis system 101 may include a predictive data analysis computing entity 106 and a storage subsystem 108. The predictive data analysis computing entity 106 may be configured to receive predictive data analysis requests from one or more external computing entities 102, process the predictive data analysis requests to generate predictions corresponding to the predictive data analysis requests, provide the generated predictions to the external computing entities 102, and automatically perform prediction-based actions based at least in part on the generated predictions.

The storage subsystem 108 may be configured to store input data used by the predictive data analysis computing entity 106 to perform predictive data analysis as well as model definition data used by the predictive data analysis computing entity 106 to perform various predictive data analysis tasks. The storage subsystem 108 may include one or more storage units, such as multiple distributed storage units that are connected through a computer network. Each storage unit in the storage subsystem 108 may store at least one of one or more data assets and/or one or more data about the computed properties of one or more data assets. Moreover, each storage unit in the storage subsystem 108 may include one or more non-volatile storage or memory media including, but not limited to, hard disks, ROM, PROM, EPROM, EEPROM, flash memory, MMCs, SD memory cards, Memory Sticks, CBRAM, PRAM, FeRAM, NVRAM, MRAM, RRAM, SONOS, FJG RAM, Millipede memory, racetrack memory, and/or the like.

Exemplary Predictive Data Analysis Computing Entity

FIG. 2 provides a schematic of a predictive data analysis computing entity 106 according to one embodiment of the present invention. In general, the terms computing entity, computer, entity, device, system, and/or similar words used herein interchangeably may refer to, for example, one or more computers, computing entities, desktops, mobile phones, tablets, phablets, notebooks, laptops, distributed systems, kiosks, input terminals, servers or server networks, blades, gateways, switches, processing devices, processing entities, set-top boxes, relays, routers, network access points, base stations, the like, and/or any combination of devices or entities adapted to perform the functions, operations, and/or processes described herein. Such functions, operations, and/or processes may include, for example, transmitting, receiving, operating on, processing, displaying, storing, determining, creating/generating, monitoring, evaluating, comparing, and/or similar terms used herein interchangeably. In one embodiment, these functions, operations, and/or processes can be performed on data, content, information, and/or similar terms used herein interchangeably.

As indicated, in one embodiment, the predictive data analysis computing entity 106 may also include one or more communications interfaces 220 for communicating with various computing entities, such as by communicating data, content, information, and/or similar terms used herein interchangeably that can be transmitted, received, operated on, processed, displayed, stored, and/or the like.

As shown in FIG. 2, in one embodiment, the predictive data analysis computing entity 106 may include, or be in communication with, one or more processing elements 205 (also referred to as processors, processing circuitry, and/or similar terms used herein interchangeably) that communicate with other elements within the predictive data analysis computing entity 106 via a bus, for example. As will be understood, the processing element 205 may be embodied in a number of different ways.

For example, the processing element 205 may be embodied as one or more complex programmable logic devices (CPLDs), microprocessors, multi-core processors, coprocessing entities, application-specific instruction-set processors (ASIPs), microcontrollers, and/or controllers. Further, the processing element 205 may be embodied as one or more other processing devices or circuitry. The term circuitry may refer to an entirely hardware embodiment or a combination of hardware and computer program products. Thus, the processing element 205 may be embodied as integrated circuits, application specific integrated circuits (ASICs), field programmable gate arrays (FPGAs), programmable logic arrays (PLAs), hardware accelerators, other circuitry, and/or the like.

As will therefore be understood, the processing element 205 may be configured for a particular use or configured to execute instructions stored in volatile or non-volatile media or otherwise accessible to the processing element 205. As such, whether configured by hardware or computer program products, or by a combination thereof, the processing element 205 may be capable of performing steps or operations according to embodiments of the present invention when configured accordingly.

In one embodiment, the predictive data analysis computing entity 106 may further include, or be in communication with, non-volatile media (also referred to as non-volatile storage, memory, memory storage, memory circuitry and/or similar terms used herein interchangeably). In one embodiment, the non-volatile storage or memory may include one or more non-volatile storage or memory media 210, including, but not limited to, hard disks, ROM, PROM, EPROM, EEPROM, flash memory, MMCs, SD memory cards, Memory Sticks, CBRAM, PRAM, FeRAM, NVRAM, MRAM, RRAM, SONOS, FJG RAM, Millipede memory, racetrack memory, and/or the like.

As will be recognized, the non-volatile storage or memory media may store databases, database instances, database management systems, data, applications, programs, program modules, scripts, source code, object code, byte code, compiled code, interpreted code, machine code, executable instructions, and/or the like. The term database, database instance, database management system, and/or similar terms used herein interchangeably may refer to a collection of records or data that is stored in a computer-readable storage medium using one or more database models, such as a hierarchical database model, network model, relational model, entity-relationship model, object model, document model, semantic model, graph model, and/or the like.

In one embodiment, the predictive data analysis computing entity 106 may further include, or be in communication with, volatile media (also referred to as volatile storage, memory, memory storage, memory circuitry and/or similar terms used herein interchangeably). In one embodiment, the volatile storage or memory may also include one or more volatile storage or memory media 215, including, but not limited to, RAM, DRAM, SRAM, FPM DRAM, EDO DRAM, SDRAM, DDR SDRAM, DDR2 SDRAM, DDR3 SDRAM, RDRAM, TTRAM, T-RAM, Z-RAM, RIMM, DIMM, SIMM, VRAM, cache memory, register memory, and/or the like.

As will be recognized, the volatile storage or memory media may be used to store at least portions of the databases, database instances, database management systems, data, applications, programs, program modules, scripts, source code, object code, byte code, compiled code, interpreted code, machine code, executable instructions, and/or the like being executed by, for example, the processing element 205. Thus, the databases, database instances, database management systems, data, applications, programs, program modules, scripts, source code, object code, byte code, compiled code, interpreted code, machine code, executable instructions, and/or the like may be used to control certain aspects of the operation of the predictive data analysis computing entity 106 with the assistance of the processing element 205 and operating system.

As indicated, in one embodiment, the predictive data analysis computing entity 106 may also include one or more communications interfaces 220 for communicating with various computing entities, such as by communicating data, content, information, and/or similar terms used herein interchangeably that can be transmitted, received, operated on, processed, displayed, stored, and/or the like. Such communication may be executed using a wired data transmission protocol, such as fiber distributed data interface (FDDI), digital subscriber line (DSL), Ethernet, asynchronous transfer mode (ATM), frame relay, data over cable service interface specification (DOCSIS), or any other wired transmission protocol. Similarly, the predictive data analysis computing entity 106 may be configured to communicate via wireless external communication networks using any of a variety of protocols, such as general packet radio service (GPRS), Universal Mobile Telecommunications System (UMTS), Code Division Multiple Access 2000 (CDMA2000), CDMA2000 1X (1xRTT), Wideband Code Division Multiple Access (WCDMA), Global System for Mobile Communications (GSM), Enhanced Data rates for GSM Evolution (EDGE), Time Division-Synchronous Code Division Multiple Access (TD-SCDMA), Long Term Evolution (LTE), Evolved Universal Terrestrial Radio Access Network (E-UTRAN), Evolution-Data Optimized (EVDO), High Speed Packet Access (HSPA), High-Speed Downlink Packet Access (HSDPA), IEEE 802.11 (Wi-Fi), Wi-Fi Direct, 802.16 (WiMAX), ultra-wideband (UWB), infrared (IR) protocols, near field communication (NFC) protocols, Wibree, Bluetooth protocols, wireless universal serial bus (USB) protocols, and/or any other wireless protocol.

Although not shown, the predictive data analysis computing entity 106 may include, or be in communication with, one or more input elements, such as a keyboard input, a mouse input, a touch screen/display input, motion input, movement input, audio input, pointing device input, joystick input, keypad input, and/or the like. The predictive data analysis computing entity 106 may also include, or be in communication with, one or more output elements (not shown), such as audio output, video output, screen/display output, motion output, movement output, and/or the like.

Exemplary External Computing Entity

FIG. 3 provides an illustrative schematic representative of an external computing entity 102 that can be used in conjunction with embodiments of the present invention. In general, the terms device, system, computing entity, entity, and/or similar words used herein interchangeably may refer to, for example, one or more computers, computing entities, desktops, mobile phones, tablets, phablets, notebooks, laptops, distributed systems, kiosks, input terminals, servers or server networks, blades, gateways, switches, processing devices, processing entities, set-top boxes, relays, routers, network access points, base stations, the like, and/or any combination of devices or entities adapted to perform the functions, operations, and/or processes described herein. External computing entities 102 can be operated by various parties. As shown in FIG. 3, the external computing entity 102 can include an antenna 312, a transmitter 304 (e.g., radio), a receiver 306 (e.g., radio), and a processing element 308 (e.g., CPLDs, microprocessors, multi-core processors, coprocessing entities, ASIPs, microcontrollers, and/or controllers) that provides signals to and receives signals from the transmitter 304 and receiver 306, correspondingly.

The signals provided to and received from the transmitter 304 and the receiver 306, correspondingly, may include signaling information/data in accordance with air interface standards of applicable wireless systems. In this regard, the external computing entity 102 may be capable of operating with one or more air interface standards, communication protocols, modulation types, and access types. More particularly, the external computing entity 102 may operate in accordance with any of a number of wireless communication standards and protocols, such as those described above with regard to the predictive data analysis computing entity 106. In a particular embodiment, the external computing entity 102 may operate in accordance with multiple wireless communication standards and protocols, such as UMTS, CDMA2000, 1xRTT, WCDMA, GSM, EDGE, TD-SCDMA, LTE, E-UTRAN, EVDO, HSPA, HSDPA, Wi-Fi, Wi-Fi Direct, WiMAX, UWB, IR, NFC, Bluetooth, USB, and/or the like. Similarly, the external computing entity 102 may operate in accordance with multiple wired communication standards and protocols, such as those described above with regard to the predictive data analysis computing entity 106 via a network interface 320.

Via these communication standards and protocols, the external computing entity 102 can communicate with various other entities using concepts such as Unstructured Supplementary Service Data (USSD), Short Message Service (SMS), Multimedia Messaging Service (MIMS), Dual-Tone Multi-Frequency Signaling (DTMF), and/or Subscriber Identity Module Dialer (SIM dialer). The external computing entity 102 can also download changes, add-ons, and updates, for instance, to its firmware, software (e.g., including executable instructions, applications, program modules), and operating system.

According to one embodiment, the external computing entity 102 may include location determining aspects, devices, modules, functionalities, and/or similar words used herein interchangeably. For example, the external computing entity 102 may include outdoor positioning aspects, such as a location module adapted to acquire, for example, latitude, longitude, altitude, geocode, course, direction, heading, speed, universal time (UTC), date, and/or various other information/data. In one embodiment, the location module can acquire data, sometimes known as ephemeris data, by identifying the number of satellites in view and the relative positions of those satellites (e.g., using global positioning systems (GPS)). The satellites may be a variety of different satellites, including Low Earth Orbit (LEO) satellite systems, Department of Defense (DOD) satellite systems, the European Union Galileo positioning systems, the Chinese Compass navigation systems, Indian Regional Navigational satellite systems, and/or the like. This data can be collected using a variety of coordinate systems, such as the Decimal Degrees (DD); Degrees, Minutes, Seconds (DMS); Universal Transverse Mercator (UTM); Universal Polar Stereographic (UPS) coordinate systems; and/or the like. Alternatively, the location information/data can be determined by triangulating the external computing entity's 102 position in connection with a variety of other systems, including cellular towers, Wi-Fi access points, and/or the like. Similarly, the external computing entity 102 may include indoor positioning aspects, such as a location module adapted to acquire, for example, latitude, longitude, altitude, geocode, course, direction, heading, speed, time, date, and/or various other information/data. Some of the indoor systems may use various position or location technologies including RFID tags, indoor beacons or transmitters, Wi-Fi access points, cellular towers, nearby computing devices (e.g., smartphones, laptops) and/or the like. For instance, such technologies may include the iBeacons, Gimbal proximity beacons, Bluetooth Low Energy (BLE) transmitters, NFC transmitters, and/or the like. These indoor positioning aspects can be used in a variety of settings to determine the location of someone or something to within inches or centimeters.

The external computing entity 102 may also comprise a user interface (that can include a display 316 coupled to a processing element 308) and/or a user input interface (coupled to a processing element 308). For example, the user interface may be a user application, browser, user interface, and/or similar words used herein interchangeably executing on and/or accessible via the external computing entity 102 to interact with and/or cause display of information/data from the predictive data analysis computing entity 106, as described herein. The user input interface can comprise any of a number of devices or interfaces allowing the external computing entity 102 to receive data, such as a keypad 318 (hard or soft), a touch display, voice/speech or motion interfaces, or other input device. In embodiments including a keypad 318, the keypad 318 can include (or cause display of) the conventional numeric (0-9) and related keys (#, *), and other keys used for operating the external computing entity 102 and may include a full set of alphabetic keys or set of keys that may be activated to provide a full set of alphanumeric keys. In addition to providing input, the user input interface can be used, for example, to activate or deactivate certain functions, such as screen savers and/or sleep modes.

The external computing entity 102 can also include volatile storage or memory 322 and/or non-volatile storage or memory 324, which can be embedded and/or may be removable. For example, the non-volatile memory may be ROM, PROM, EPROM, EEPROM, flash memory, MMCs, SD memory cards, Memory Sticks, CBRAM, PRAM, FeRAM, NVRAM, MRAM, RRAM, SONOS, FJG RAM, Millipede memory, racetrack memory, and/or the like. The volatile memory may be RAM, DRAM, SRAM, FPM DRAM, EDO DRAM, SDRAM, DDR SDRAM, DDR2 SDRAM, DDR3 SDRAM, RDRAM, TTRAM, T-RAM, Z-RAM, RIMM, DIMM, SIMM, VRAM, cache memory, register memory, and/or the like. The volatile and non-volatile storage or memory can store databases, database instances, database management systems, data, applications, programs, program modules, scripts, source code, object code, byte code, compiled code, interpreted code, machine code, executable instructions, and/or the like to implement the functions of the external computing entity 102. As indicated, this may include a user application that is resident on the entity or accessible through a browser or other user interface for communicating with the predictive data analysis computing entity 106 and/or various other computing entities.

In another embodiment, the external computing entity 102 may include one or more components or functionality that are the same or similar to those of the predictive data analysis computing entity 106, as described in greater detail above. As will be recognized, these architectures and descriptions are provided for exemplary purposes only and are not limiting to the various embodiments.

In various embodiments, the external computing entity 102 may be embodied as an artificial intelligence (AI) computing entity, such as an Amazon Echo, Amazon Echo Dot, Amazon Show, Google Home, and/or the like. Accordingly, the external computing entity 102 may be configured to provide and/or receive information/data from a user via an input/output mechanism, such as a display, a camera, a speaker, a voice-activated input, and/or the like. In certain embodiments, an AI computing entity may comprise one or more predefined and executable program algorithms stored within an onboard memory storage module, and/or accessible over a network. In various embodiments, the AI computing entity may be configured to retrieve and/or execute one or more of the predefined program algorithms upon the occurrence of a predefined trigger event.

V. Exemplary System Operations

Various embodiments of the present invention introduce techniques for training ARIMA models to perform seasonally-adjusted predictive data analysis operations. In the description below, aspects of the ARIMA model training concepts of the present invention are described in Subsection A, while aspects of the ARIMA-based predictive inference concepts of the present invention are described in Subsection B.

However, while various embodiments of the present invention describe the ARIMA model training concepts of the present invention and the ARIMA-based predictive inference concepts of the present invention as being performed by a single computing entity (e.g., by the predictive data analysis computing entity 106), a person of ordinary skill in the relevant technology will recognize that each of the ARIMA model training concepts of the present invention and the ARIMA-based predictive inference concepts of the present invention may be performed by a system of one or more computers that is distinct and potentially remote from a system of one or more computers used to practice the other aspect of various embodiments of the present invention.

A. Generating a Trained ARIMA Model

FIG. 4 is a flowchart diagram of an example process 400 for generating a trained ARIMA model that is configured to perform seasonally-adjusted predictive data analysis. Via the various steps/operations of the process 400, the predictive data analysis computing entity 106 can integrate seasonal adjustments into ARIMA models by performing seasonal adjustments on inputs of those models, a relatively efficient approach for integrating seasonality adjustment into ARIMA models that in turn improves the computational efficiency of computer-implemented processes for training ARIMA models by reducing the need for performing computationally resource-intensive differencing operations.

The process 400 begins at step/operation 401 when the predictive data analysis computing entity 106 generates a group of raw input data entries. The raw input data entries may describe a monitored state of an observed phenomenon over a monitored period of time. For example, the raw input data entries may describe the percentage of flu patients over a predefined number of weeks in a particular geographic region (e.g., a particular state, a particular metropolitan area, and/or the like). In some embodiments, the predictive data analysis computing entity 106 may generate the group of raw input data entries based at least in part on data describing various underlying metrics of the observed phenomenon. For example, if the raw input data entries describe the estimated percentage of flu patients over a predefined number of weeks in a particular geographic region, the noted raw input data entries may be determined based at least in part on the medical claim data (e.g., health insurance claim data) associated with the particular geographic region during the predefined number of weeks.

In general, a raw input data entry may describe a monitored state of an observed phenomenon over a corresponding unit of time, where the observed phenomenon may be associated with a particular geographic region. Collectively, a group of raw input data entries may describe the monitored state of two or more observed phenomena over many periods of times, where each of the two or more observed phenomena may relate to a geographic region of a group of a geographic regions, and where the group of geographic regions may include at least two geographic regions that are overlapping (e.g., a geographic region of New York City metropolitan area and a geographic region of the state of New York). In some embodiments, a raw input data entry describes an estimated percentage of flu patients in a corresponding geographic region during a corresponding week. In some of the noted embodiments, the group of raw input data entries may describe estimated percentages of flu patients across many geographic regions (which may include overlapping geographic regions) across a group of weeks during a historical monitored period (e.g., a historical monitored period between 2014 and 2019).

In some embodiments, the estimated percentage of flu patients for a corresponding geographic region during a corresponding time period may be determined based at least in part on a ratio of: (i) a number of flu-related medical claims for the corresponding geographic region during the corresponding time period; and (ii) a total number of medical claims for the corresponding geographic region during the corresponding time period. In some embodiments, determining whether a medical claim is a flu-related medical claim is performed in accordance with a determination about whether a diagnosis code designation of the medical claim describes that the medical claim is flu-related. For example, in some embodiments, at least the following diagnosis codes may be determined flu-related: International Classification of Diseases, Ninth Revision, Clinical Modification (ICD-9-CM) codes 480-488 and International Classification of Diseases, Tenth Revision, Clinical Modification (ICD-10-CM) codes J09-J18.

In some embodiments, determining whether a medical claim relates to a geographic region is performed in accordance with a determination about whether a place of service code for the medical claim describes the geographic region, where the place of service codes for various geographic region may be described in accordance with place of service codes defined for the Health Care Finance Administration (HCFA) 1500 form as defined by the Centers for Medicare & Medicaid Services (CMS). In some embodiments, determining whether a medical claim relates to a geographic region is performed in accordance with a determination about whether a zip code for the medical claim describes the geographic region. For example, in some embodiments, the predictive data analysis computing entity 106 may determine that a medical claim relates to Atlanta-Sandy Springs-Alpharetta metropolitan statistical area (MSA) if the zip code for the medical claim begins with 300, 301, 302, 303, 305, or 306.

At step/operation 402, the predictive data analysis computing entity 106 performs one or more input data transformation operations on the group of raw input data entries to generate a transformed input timeseries data object. One goal of the input data transformation operations may be to remove outlier values from the group of raw input data entries and/or to stabilize variance of the group of raw input data entries across time. In some embodiments, performing the input data transformation on a group of raw input data entries operations comprises performing seasonal averaging operations on the group of raw input data entries outlier replacement followed by logarithmic variance stabilization operations on the output of the seasonal averaging operations.

In some embodiments, step/operation 402 may be performed in accordance with the process depicted in FIG. 5. The process depicted in FIG. 5 begins at step/operation 501 when the predictive data analysis computing entity 106 performs seasonal averaging outlier replacement on the group of raw input data entries to generate a group of seasonally averaged input data entries. In some embodiments, to perform the seasonal averaging outlier replacement on the group of raw input data entries, the predictive data analysis computing entity 106 determines, for each raw input data entry in a particular inferior time period of a superior time period for a particular geographic region, whether the raw input data entry represents an outlier value in accordance with a distribution of the raw data entries for the particular inferior time period and the particular geographic region across all superior time periods. If the predictive data analysis computing entity 106 determines that the raw input data entry represents an outlier value in accordance with the noted distribution for the particular inferior time period and the particular geographic region, the predictive data analysis computing entity 106 updates the raw input data entry based at least in part on an average of the noted distribution.

In some embodiments, for a particular raw input data entry, step/operation 501 may be performed in accordance with the process depicted in FIG. 6. The process depicted in FIG. 6 begins at step/operation 601 when the predictive data analysis computing entity 106 identifies an inferior time period, a superior time period, and a geographic region for the particular raw input data entry. For example, the predictive data analysis computing entity 106 may determine that the particular raw input data entry is associated with the $12^{th}$ week of the year 2019 for the Atlanta-Sandy Springs-Alpharetta MSA.

In general, an inferior time period may describe a time period that is deemed to be a subcomponent of a superior time period in a manner that the temporal position of the inferior time period within the superior time period describes an expected pattern of seasonality for the overall timeseries data so that significant deviations between common inferior time periods across different superior time periods may be deemed less statistically significant. Examples of inferior time periods may include weeks, months, or seasons, while examples of superior time periods may include years. In an exemplary embodiments, a year may be expected to display seasonality patterns that in turn causes particular weeks/months/seasons of the year to show an expected level of consistency across years, an assumption that in turn causes significant deviations from cross-annual distributions for the raw input data entry of a particular week/month/season to be deemed less statistically significant and thus replaceable. (e.g., if the raw input data entry for week n differs significantly from the average value for week n across all years in a monitored period, the raw input data entry for week n may be deemed less statistically significant and thus replaceable).

Similarly, a superior time period may describe a time period that is deemed to include two or more inferior time periods characterized by a temporal ordering that assigns a temporal position to each of the noted inferior time periods, where the temporal ordering describes an expected pattern of seasonality for the overall timeseries data in a manner that makes significant deviations between common inferior time periods across different superior time periods deemed less statistically significant. As noted above, an example of a superior time period may describe a year, which may include various inferior time periods (e.g., 4 seasons, 12 months, 52 weeks, 2 half-years, and/or the like), where the temporal position of each inferior time period is expected to prescribe an expected level of consistency for the raw input data entry values for the inferior time period across multiple years, an assumption that in turn causes significant deviations from cross-annual distributions for the raw input data entry of a particular inferior time period to be deemed less statistically significant and thus replaceable.

At step/operation 602, the predictive data analysis computing entity 106 generates a target distribution for the raw input data entries based at least in part on each raw input data entry for the particular inferior time unit across all superior time units associated with the group of raw input data entries in relation to the particular geographic region. For example, given a group of raw input data entries that include week-level flu patient percentages for various geographic regions across the years 2014-2019, and given a particular raw input data entry that describes the week-level flu patient percentage for week 12 of the year 2019 in relation to the Atlanta-Sandy Springs-Alpharetta MSA, the target distribution may describe a statistical distribution of each week-level flu patient percentage that in turn describes: (i) the week-level flu patient percentage for week 12 of the year 2014 in relation to the Atlanta-Sandy Springs-Alpharetta MSA, (ii) the week-level flu patient percentage for week 12 of the year 2015 in relation to the Atlanta-Sandy Springs-Alpharetta MSA, (iii) the week-level flu patient percentage for week 12 of the year 2016 in relation to the Atlanta-Sandy Springs-Alpharetta MSA, (iv) the week-level flu patient percentage for week 12 of the year 2017 in relation to the Atlanta-Sandy Springs-Alpharetta MSA, (v) the week-level flu patient percentage for week 12 of the year 2018 in relation to the Atlanta-Sandy Springs-Alpharetta MSA, and (vi) the week-level flu patient percentage for week 12 of the year 2019 in relation to the Atlanta-Sandy Springs-Alpharetta MSA.

At step/operation 603, the predictive data analysis computing entity 106 generates an average of the target distribution. However, while various embodiments of the present invention describe performing outlier replacement using averaging operations, a person of ordinary skill in the art will recognize that other measures of statistical distribution (e.g., median, mode, a weighted average) of the target distribution can be used to update a particular raw input data entry that is associated with an outlier region of the target distribution.

At step/operation 604, the predictive data analysis computing entity 106 determines whether the particular raw input data entry is within an outlier region of the target distribution. In some embodiments, the predictive data analysis computing entity 106 determines whether the particular raw input data entry is within an outlier region of the target distribution based at least in part on an outlier region boundary determination parameter that describes a number of standard deviations of the target distribution from the average value for the target distribution that define the outer limits for the tail-end subregions of the outlier region of the target distribution. In some embodiments, the outlier region determination parameter may be a predefined parameter provided by an administrator user profile of the predictive data analysis system 101, a runtime-provided parameter supplied by the administrator user profile of the predictive data analysis system 101, a trained parameter determined using a trained outlier region determination machine learning model, and/or the like.

At step/operation 605, in response to determining that the particular raw input data entry is within the outlier region of the target distribution, the predictive data analysis computing entity 106 updates the particular raw input data entry based at least in part on the average of the target distribution. Moreover, at step/operation 606, in response to determining that the particular raw input data entry is not within the outlier region of the target distribution, the predictive data analysis computing entity 106 does not update the particular raw input data entry. However, as previously discussed, while various embodiments of the present invention describe performing outlier replacement using averaging operations, a person of ordinary skill in the art will recognize that other measures of statistical distribution (e.g., median, mode, a weighted average) of the target distribution can be used to update a particular raw input data entry that is associated with an outlier region of the target distribution.

In some embodiments, to update the particular raw input data entry based at least in part on the average of the target distribution, the predictive data analysis computing entity 106 replaces the particular raw input data entry with the average of the target distribution. In some embodiments, to update the particular raw input data entry based at least in part on the average of the target distribution, the predictive data analysis computing entity 106 replaces the particular raw input data entry with an average of: (i) the original value of the particular raw input data entry, and (ii) the average of the target distribution. In some embodiments, to update the particular raw input data entry based at least in part on the average of the target distribution, the predictive data analysis computing entity 106 replaces the particular raw input data entry with a value determined by supplying the particular raw input data entry and the average of the target distribution to a trained outlier replacement machine learning model.

Returning to FIG. 5, at step/operation 502, the predictive data analysis computing entity 106 performs logarithmic variance stabilization on the group of seasonally averaged input data entries to generate a group of variance-stabilized input data entries. In some embodiments, to perform logarithmic variance stabilization, the predictive data analysis computing entity 106 applies a logarithmic transformation to the group of seasonally averaged input data entries in order to ensure that the variance of the group of seasonally averaged input data entries is constant, and not a function of the average of the group of seasonally averaged input data entries. In some embodiments, performing variance stabilization on input data may reduce the need to select models that reduce stationarity of input data using computationally expensive differencing operations, a feature that helps reduce both the training efficiency of untrained ARIMA models and inference efficiency of ARIMA models.

An operational example of a logarithmic variance stabilization operation 700 is depicted in FIG. 7. As depicted in FIG. 7, the logarithmic variance stabilization operation 700 processes a non-stationary timeseries data object 701 (e.g., a non-stationary timeseries data object 701 describing the group of seasonally averaged input data entries) to generate a variance-stabilized timeseries data object 702 (e.g., a variance-stabilized timeseries data object 702 describing the group of variance-stabilized input data entries), where the variance-stabilized timeseries data object 702 has a more stable variance and a higher degree of stationarity relative to the non-stationary timeseries data object 701. As noted above, generating the variance-stabilized timeseries data object 702 which has a higher degree of stationarity relative to the non-stationary timeseries data object 701 can reduce the need for performing computationally expensive differencing operations and thus reduce both the training efficiency of untrained ARIMA models and inference efficiency of ARIMA models.

Returning to FIG. 5, at step/operation 503, the predictive data analysis computing entity 106 generates the transformed input timeseries data object based at least in part on the group of variance-stabilized input data entries. In some embodiments, the predictive data analysis computing entity 106 adopts the group of variance-stabilized input data entries as the transformed input timeseries data object. In some embodiments, the predictive data analysis computing entity 106 performs one or more additional input data transformation operations (i.e., one or more input data transformation operations in addition to the seasonal averaging outlier replacement operation and the logarithmic variance-stabilization operation) in order to generate the transformed input timeseries data object. In general, the transformed input timeseries data object may describe the output data object that results from performing one or more input data transformation operations on a group of input data entities.

Returning to FIG. 4, at step/operation 403, the predictive data analysis computing entity 106 generates a training input timeseries data object and a testing input timeseries data object based at least in part on the transformed input timeseries data object. In some embodiments, to generate the training input timeseries data object and the testing timeseries data object, the predictive data analysis computing entity 106 divides a monitoring window associated with the transformed input timeseries data object into a training window and a testing window, assigns a subset of the transformed input timeseries data object that relates to the training window to the training input timeseries data object, and assigns a subset of the transformed input timeseries data object that relates to the testing window to the testing input timeseries data object. For example, given a monitoring window that includes the years 2014-2019, the predictive data analysis computing entity 106 may determine that the last 48 weeks of the monitoring window describe the testing window, while the rest of the monitoring window describe the training period. Therefore, in accordance with the noted example, the predictive data analysis computing entity 106 may determine that the training window covers the period from the first week of 2014 to the fourth week of 2019, while the testing window covers the period from the fifth week of 2019 to the last week of 2019.

In general, in some embodiments, the testing window may be determined based at least in part on a number of inferior time periods at the end of the monitoring window and/or a ratio of inferior time periods of the monitoring window that occur at the end of the monitoring window, where the noted number and/or ratio may be determined based at least in part on at least one of a predefined parameter provided by an administrator user profile of the predictive data analysis system 101, a runtime-provided parameter supplied by the administrator user profile of the predictive data analysis system 101, a trained parameter determined using a trained monitoring window division machine learning model, and/or the like.

At step/operation 404, the predictive data analysis computing entity 106 generates a seasonally adjusted training input timeseries data object based at least in part on the training input timeseries data object. In some embodiments, in order to generate the training input timeseries data object, the predictive data analysis computing entity 106 removes a seasonality component of the training input timeseries data object from the training input timeseries data object. To do so, the predictive data analysis computing entity 106 may process the training input timeseries data object in order to generate a trend component, a seasonality component, and an error component of the training input timeseries data object. For example, as depicted in FIG. 9, the predictive data analysis computing entity 106 has processed the training input timeseries data object 901 to generate the trend component 911 of the training input timeseries data object 901, the seasonality component 912 of the training input timeseries data object 901, and the error component 913 of the training input timeseries data object 901.

In some embodiments, step/operation 404 may be performed in accordance with the process described in FIG. 8.

The process depicted in FIG. 8 begins at step/operation 801 when the predictive data analysis computing entity generates a trend component of the training input timeseries data object. In general, a trend component of a timeseries data object may describe long-term increases or decreases in the timeseries data object across the totality of the time window associated with the timeseries data object. In some embodiments, to generate the trend component of a timeseries data object, the predictive data analysis computing entity 106 performs a smoothing operation on the timeseries data object in a manner configured to represent buckets of timeseries data object values by a single representative value. For example, in some embodiments, to perform the noted smoothing operation, the predictive data analysis computing entity 106 may apply local weighted regression on the timeseries data object. An example bucket size for a smoothing operation that can be performed as part of a trend generation process is a bucket size that describes 52 contiguous data entries of the noted timeseries data object.

At step/operation 802, the predictive data analysis computing entity 106 generates a seasonality component of the training input timeseries data object. In general, a seasonality component of a timeseries data object may describe short-term fluctuations of the timeseries data object across portions of the timeseries data object that relate to particular superior time periods (e.g., particular years). In some embodiments, given a timeseries data object that includes x inferior time periods (e.g., 52 weeks) of L superior time periods (e.g., ten years), the seasonality of the training input timeseries data object is determined by determining, for each of the x inferior time periods, a seasonality value based at least in part on a measure of statistical distribution (e.g., an average) of the timeseries data object values for the inferior time period across all of the L superior time periods (e.g., by calculating $[i+(i+(i+2x)+ \ldots +(i+Lx)]/L$, where i describes the particular inferior time period of a first superior time period in the monitoring window, such as a particular week of a first year of the monitoring window).

At step/operation 803, the predictive data analysis computing entity 106 generates an error component of the training input timeseries data object. In general, an error component of a timeseries data object may describe the residual value generated after subtracting the trend component of the timeseries data object and the seasonality component of the timeseries data object from the noted timeseries data object. Accordingly, the error component of a timeseries data object may describe variations in the timeseries data object not captured by either the long-term movements of the timeseries data object as represented by the trend component of the timeseries data object, or the short-term fluctuations of the timeseries data object as represented by the error component of the timeseries data object.

At step/operation 804, the predictive data analysis computing entity 106 generates the seasonally adjusted training input timeseries data object based at least in part on the trend component of the training input timeseries data object and the error component of the training input timeseries data object. In some embodiments, to generate the seasonally adjusted training input timeseries data object, the predictive data analysis computing entity removes (e.g., subtracts) the seasonality component of the training input timeseries data object. In some embodiments, to generate the seasonally adjusted training input timeseries data object, the predictive data analysis computing entity 106 combines (e.g., aggregates) the trend component of the training input timeseries data object and the error component of the training input timeseries data object.

Returning to FIG. 4, at step/operation 405, the predictive data analysis computing entity 106 generates the trained ARIMA model based at least in part on the seasonally-adjusted training input timeseries data object. In general, to generate the trained ARIMA model, the predictive data analysis computing entity 106 determines optimal values for hyper-parameters of the ARIMA model, parameters of the ARIMA model, and covariates of the ARIMA model.

In general, a hyper-parameter of an ARIMA model describes an aspect of the number of autoregressive operations of the ARIMA model, the number of differencing operations of the ARIMA model, or the number of lagged forecast error adjustment operations of the ARIMA model. In particular, if the ARIMA model is a non-seasonal ARIMA model, the hyper-parameters of the ARIMA model may include: (i) p, which describes the number of autoregressive terms of the ARIMA model and is also known as the lag order hyper-parameter of the ARIMA model; (ii) d, which describes the number of non-seasonal differencing operations performed to make the data stationary, and is also known as the differencing order hyper-parameter of the ARIMA mode; and (iii) q, which describes the number of lagged forecast error adjustment operations of the ARIMA model, and is also known as the moving average order of the ARIMA model. Moreover, if the ARIMA model is a seasonal ARIMA model, the hyper-parameters of the ARIMA model may include: (i) p, which describes the number of autoregressive terms of the ARIMA model and is also known as the lag order hyper-parameter of the ARIMA model; (ii) d, which describes the number of non-seasonal differencing operations performed to make the data stationary, and is also known as the differencing order hyper-parameter of the ARIMA mode; (iii) q, which describes the number of lagged forecast error adjustment operations of the ARIMA model, and is also known as the moving average order of the ARIMA model; (iv) P, which describes the number of seasonal autoregressive terms of the ARIMA model and is also known as the seasonal lag order hyper-parameter of the ARIMA model; (v) D, which describes the number of seasonal differencing operations performed to make the data stationary, and is also known as the seasonal differencing order hyper-parameter of the ARIMA mode; and (vi) Q, which describes the number of seasonal lagged forecast error adjustment operations of the ARIMA model, and is also known as the seasonal moving average order of the ARIMA model.

Furthermore, a covariate of an ARIMA model may describe a value supplied as part of a linear term of the ARIMA model, where the noted value is configured to describe an observed/forecasted state of a target phenomenon during a time period that occurs subsequent to a time period associated with a current iteration of the ARIMA model. For example, consider an ARIMA model that has a first covariate describing a one-week-lagged prospective flu patient percentage, a second covariate describing a two-week-lagged prospective flu patient percentage, and a third covariate describing a three-week-lagged prospective flu patient percentage. In the noted example, during a testing iteration of the noted ARIMA model that is associated with week 20 of 2018, the values of the three covariates may be determined based at least in part on historical data about flu patient percentages of weeks 21-23 of 2018 respectively; however, during a prediction iteration of the noted ARIMA model that is associated with week 20 of 2021, the values of three covariates may be estimated based at least in part on trained parameters of the model and may at least a part of the predictive output of running the trained ARIMA model on a predictive inference iteration associated with week 20 of 2018. Thus, according to the latter scenario (i.e., the prediction iteration), the values of the covariates may be used to determine prospective time-lagged predictions that may be outputs of a trained ARIMA model.

Moreover, a parameter of an ARIMA model may describe any value that is determined during training of the ARIMA model but is not a hyper-parameter of the ARIMA model. For example, parameters of the ARIMA model may include coefficients applied to hyper-parameters of the ARIMA model and/or applied to covariates of the ARIMA model as part of the linear operations of the ARIMA model. In some embodiments, training of an ARIMA model includes determining optimal values for parameters of the ARIMA model subsequent to determining optimal values for hyper-parameters of the ARIMA model.

An example of a trained ARIMA model is the influenza forecasting ARIMA model configured to perform the operations of the equation $FLU2_t = 0.3647 + 0.6694*AR1 + 0.0676*AR2 + 11.6575*FLU2t\{t,i=t+1\} - 11.3916*FLU2t\{t, i=t+2\} - 0.1867* FLU2t\{t, i=t+3\}$. The trained ARIMA model of the noted equation is a non-seasonal ARIMA model that is associated with a p value of two, a d value of zero, and a q value of zero. In the noted equation, AR1 is the first non-seasonal autoregressive term of the trained ARIMA model, AR2 is the second non-seasonal autoregressive term of the trained ARIMA model, FLU2t describes the flu patient percentage at a current time period (e.g., a current week), $FLU2t\{t,i=t+1\}$ describes the flu patient percentage after one time period following the current time period (e.g., after the week following the current week), $FLU2t \{t,i=t+2\}$ describes the flu patient percentage after two time periods following the current time period (e.g., after two weeks following the current week), and $FLU2t \{t,i=t+3\}$ describes the flu patient percentage after three time periods following the current time period (e.g., after three weeks following the current week), with the latter three terms (i.e., $FLU2t\{t,i=t+1\}$, $FLU2t\{t,i=t+2\}$, $FLU2t\{t,i=t+3\}$) being covariates of the trained ARIMA model. Furthermore, the optimal parameters of the noted ARIMA model include the following: (i) 0.3647; (ii) 0.6694, which is a coefficient applied to AR1; (iii) 0.0676, which is a coefficient applied to AR2; (iv) 11.6575, which is a coefficient applied to $FLU2t \{t,i=t+1\}$; (v) 11.3916, which is a coefficient applied to $FLU2t \{t,i=t+2\}$; and (vi) 0.1867, which is a coefficient applied to $FLU2t \{t,i=t+3\}$.

In some embodiments, step/operation 405 may be performed in accordance with the process depicted in FIG. 10. The process depicted in FIG. 10 begins at step/operation 1001 when the predictive data analysis computing entity 106 determines the optimal differencing order hyper-parameter for the trained ARIMA model. In some embodiments, to determine the optimal differencing order hyper-parameter of the trained ARIMA model, the predictive data analysis computing entity 106 selects a value for the differencing order hyper-parameter that transforms seasonally-adjusted training input timeseries data object into a stationary seasonally-adjusted training input timeseries data object. Accordingly, in the noted embodiments, the predictive data analysis computing entity 106 performs as many differencing operations as needed until the seasonally-adjusted training input timeseries data object is deemed stationary, and uses the value describing of the number of needed differencing operations as the optimal differencing hyper-parameter (i.e., the optimal value for d) for the trained ARIMA model.

At step/operation 1002, the predictive data analysis computing entity 106 determines an optimal lag order hyper-parameter of the trained ARIMA model and an optimal moving average order hyper-parameter of the trained ARIMA model. In some embodiments, to determine the optimal lag order hyper-parameter of the trained ARIMA model and the optimal moving average order hyper-parameter of the trained ARIMA model, the predictive data analysis computing entity 106 selects a combination of the optimal lag order hyper-parameter of the trained ARIMA model and the optimal moving average order hyper-parameter of the trained ARIMA model that are collectively configured to optimize a model utility measure (e.g., minimize an information criterion measure) for the trained ARIMA model. For example, to select a combination of the optimal lag order hyper-parameter of the trained ARIMA model and the optimal moving average order hyper-parameter of the trained ARIMA model that are collectively configured to optimize a model utility measure for the trained ARIMA model, the predictive data analysis computing entity 106 may iterate through various candidate combinations of possible values for the lag order hyper-parameter and the moving average order hyper-parameter, determine a model utility measure for each combination, and then select a combination that optimizes the model utility measure (e.g., minimizes an AIC measure for the trained ARIMA model, minimizes an AICc measure for the trained ARIMA model, minimizes a BIC measure for the trained ARIMA model, and/or the like).

A model utility measure for an ARIMA model may describe at least one of a measure of fitness of the forecast of the ARIMA model relative to ground-truth data and a simplicity (e.g., the number of parameters, the number of terms, and/or the like) of the ARIMA model. In some embodiments, a model utility measure for an ARIMA model may be determined based at least in part on one of the following: an AIC for the ARIMA model, an AICc for the ARIMA model, and BIC for the ARIMA model. The AIC for an ARIMA model may be determined in accordance with the equation $AIC=-2\log(L)+2(p+q+k)$, where L is the likelihood estimation of the forecast data generated by the ARIMA model and k describes existence of the intercept of the ARIMA model (such that, if k=1, then there is an intercept, and if k=0, then there is no intercept in the ARIMA model). The AICc for an ARIMA model may be determined in accordance with the equation $AICc=AIC+(2(p+q+k)(p+q+k+1))/(T-p-q-k-1)$, and the BIC for an ARIMA model may be determined in accordance with the equation $BIC=AIC+(\log(T)-2)(p+q+k)$. In some embodiments, if two or more ARIMA models have different differencing order hyper-parameters, their model utility measures can be determined using one or more structure-agnostic error measures for the noted models, such as using at least one of RMSEs for the noted models, MAPEs for the noted models, MAEs for the noted models, MPEs for the noted models, and/or the like.

In some embodiments, the hyper-parameters of the trained ARIMA model also include a count of the covariates of the trained ARIMA model. In some of the noted embodiments, the count of the number of covariates is also calculated using the process in step/operation 1002. In other words, in some embodiments, step/operation 1002 comprises determining an optimal combination of an optimal lag order hyper-parameter of the trained ARIMA model, an optimal moving average order hyper-parameter of the trained ARIMA model, and an optimal count of covariates of the trained ARIMA model that optimize a model utility measure for the trained ARIMA model. Accordingly, in some embodiments, the trained ARIMA model for one geographic region may have a different number of covariates compared to the trained ARIMA model of another geographic region, based at least in part on the structure and the distribution of the training timeseries input data of the two noted geographic regions.

At step/operation 1003, the predictive data analysis computing entity 106 generates covariates of the ARIMA model, where each covariate is associated with a prospective time period. In some embodiments, to generate covariates of the ARIMA model during training, the predictive data analysis computing entity 106 uses the transformed input timeseries object and/or historical observation data to generate prospective observations for each prospective time period. For example, given a covariate that describes a flu patient percentage after one week following a current time period for a current testing iteration, the predictive data analysis computing entity 106 uses the transformed input timeseries object and/or historical observation data to detect the flu patient percentage after one week following the current time period and uses the detected value as the covariate value.

At step/operation 1004, the predictive data analysis computing entity 106 determines optimal parameter values for the ARIMA model. In some embodiments, the predictive data analysis computing entity 106 selects parameter values that, when applied to an ARIMA model having the hyper-parameter structure determined using the techniques described in relation to step/operation 1001 and step/operation 1002, minimize a difference between a current time period forecast of the ARIMA model and the ground-truth observation of the transformed input timeseries data object for the current time period (i.e., provide a best fit for the underlying transformed training input timeseries data object). For example, to generate the optimal parameters values for the trained ARIMA model of the equation $FLU2_t=0.3647+0.6694*AR1+0.0676*AR2+11.6575*FLU2t\{t,i=t+1\}-11.3916*FLU2t\{t, i=t+2\}-0.1867*FLU2t\{t, i=t+3\}$ as described above, the predictive data analysis computing entity 106 may fit a curve that best relates $FLU2_t$ to AR1, AR2, $FLU2t\{t,i=t+1\}$, $FLU2t\{t,i=t+2\}$, and $FLU2t\{t,i=t+3\}$ in accordance with the relationships of the noted equation. It is noteworthy that the value of FLU2t, AR1, AR2, $FLU2t\{t,i=t+1\}$, $FLU2t\{t,i=t+2\}$, and $FLU2t\{t,i=t+3\}$ can be determined in accordance with the transformed input timeseries object and/or historical observation data (e.g., historical flu patient percentage observation data) prior to fitting of the model to the underlying training input timeseries data object.

At step/operation 1005, the predictive data analysis computing entity 106 generates the trained ARIMA model based at least in part on the optimal differencing order hyper-parameter, the optimal lag order hyper-parameter, the optimal moving average order hyper-parameter, and the optimal parameter values. In some embodiments, to generate the trained ARIMA model, the predictive data analysis computing entity 106 generates a model that includes a number of differencing terms equal to the optimal differencing order hyper-parameter, a number of autoregressive terms equal to the optimal lag order hyper-parameter, a number of lagged forecast error adjustment terms equal to the moving average order hyper-parameter, a number of covariate terms, as well as the optimal parameters of the trained ARIMA model as singular terms, as coefficients of the noted hyper-parameters, as coefficients of covariate values, and/or the like.

Returning to FIG. 4, at step/operation 405, the predictive data analysis computing entity 106 determines a validation determination for the trained ARIMA model based at least in part on the testing input timeseries data object generated at step/operation 403. In some embodiments, to determine the validation determination for the trained ARIMA model, the predictive data analysis computing entity 106 processes portions of the testing input timeseries data object using the trained ARIMA model to determine forecasts for other portions of the testing input timeseries data object, compares the forecasts for the forecasted portions with the observation data for noted forecasted portions to determine an accuracy measure of the trained ARIMA model, and determines that the ARIMA model has a positive validation determination if the accuracy measure of the ARIMA model satisfies an accuracy measure threshold, where the accuracy measure threshold may be provided by an administrator user profile of the predictive data analysis system 101, a runtime-provided parameter supplied by the administrator user profile of the predictive data analysis system 101, a trained parameter determined using a trained accuracy threshold determination machine learning model, and/or the like.

In some embodiments, performing testing/validation of the trained ARIMA model at step/operation 405 includes: (i) generating a seasonally adjusted testing input timeseries data object based at least in part on the testing input timeseries data object (e.g., in accordance with the techniques described in relation to step/operation 403, but applied to a testing input timeseries data object); (ii) performing a plurality of ordered testing iterations on the seasonally adjusted testing input timeseries data object (as described in greater detail below); (iii) after each ordered testing iteration, comparing the forecasted outputs of the ordered testing iteration with the observation data of the seasonally adjusted testing input timeseries data object in order to determine a per-iteration accuracy measure for the ordered testing iteration; (iv) combining each per-iteration accuracy measure for an ordered testing iteration of the plurality of ordered testing iterations in order to determine an overall accuracy measure for the trained ARIMA model; and (v) determining whether the ARIMA model has a positive validation determination based at least in part on whether the accuracy measure of the ARIMA model satisfies an accuracy measure threshold.

In some of the noted embodiments, given a testing window associated with the testing input timeseries data object that includes a number of inferior time periods (e.g., a first week of the testing window, a second week of the testing window, a third week of the testing window, and so on), an ordered testing iteration associated with a testing iteration order i may be configured to process a portion of the testing input timeseries data object associated with inferior time periods [1, i*m] of the testing window in order to forecast a portion of testing input timeseries data object associated with inferior time periods [i*m+1, i*m+1+n] of the testing window.

For example, given m=n=6, and further given a testing window that includes 48 weeks, during a first ordered testing iteration (i=1), the predictive data analysis computing entity 106 may process the portion of the testing input timeseries data object that relates to weeks 1 to 6 of the testing window to forecast the portion of the testing input timeseries data object that relates to weeks 7 to 12 of the testing window. Afterward, the predictive data analysis computing entity 106 may compare the forecasted data for weeks 7 to 12 of the testing window to the portion of the testing input timeseries data object that relates to weeks 7 to 12 of the testing window in order to determine a per-iteration accuracy measure for the first ordered testing iteration.

In the noted example, after the first ordered testing iteration, during a second ordered testing iteration (i=2), the predictive data analysis computing entity 106 may process the portion of the testing input timeseries data object that relates to weeks 1 to 12 of the testing window to forecast the portion of the testing input timeseries data object that relates to weeks 13 to 18 of the testing window. Afterward, the predictive data analysis computing entity 106 may compare the forecasted data for weeks 13 to 18 of the testing window to the portion of the testing input timeseries data object that relates to weeks 13 to 18 of the testing window in order to determine a per-iteration accuracy measure for the second ordered testing iteration.

In the noted example, after the second ordered testing iteration, during a third ordered testing iteration (i=3), the predictive data analysis computing entity 106 may process the portion of the testing input timeseries data object that relates to weeks 1 to 18 of the testing window to forecast the portion of the testing input timeseries data object that relates to weeks 19 to 24 of the testing window. Afterward, the predictive data analysis computing entity 106 may compare the forecasted data for weeks 19 to 24 of the testing window to the portion of the testing input timeseries data object that relates to weeks 19 to 24 of the testing window in order to determine a per-iteration accuracy measure for the third ordered testing iteration.

In the noted example, after the third ordered testing iteration, during a fourth ordered testing iteration (i=4), the predictive data analysis computing entity 106 may process the portion of the testing input timeseries data object that relates to weeks 1 to 24 of the testing window to forecast the portion of the testing input timeseries data object that relates to weeks 25 to 30 of the testing window. Afterward, the predictive data analysis computing entity 106 may compare the forecasted data for weeks 25 to 30 of the testing window to the portion of the testing input timeseries data object that relates to weeks 25 to 30 of the testing window in order to determine a per-iteration accuracy measure for the fourth ordered testing iteration.

In the noted example, after the fourth ordered testing iteration, during a fifth ordered testing iteration (i=5), the predictive data analysis computing entity 106 may process the portion of the testing input timeseries data object that relates to weeks 1 to 30 of the testing window to forecast the portion of the testing input timeseries data object that relates to weeks 31 to 36 of the testing window. Afterward, the predictive data analysis computing entity 106 may compare the forecasted data for weeks 31 to 36 of the testing window to the portion of the testing input timeseries data object that relates to weeks 31 to 36 of the testing window in order to determine a per-iteration accuracy measure for the fifth ordered testing iteration.

In the noted example, after the fifth ordered testing iteration, during a sixth ordered testing iteration (i=6), the predictive data analysis computing entity 106 may process the portion of the testing input timeseries data object that relates to weeks 1 to 36 of the testing window to forecast the portion of the testing input timeseries data object that relates to weeks 36 to 42 of the testing window. Afterward, the predictive data analysis computing entity 106 may compare the forecasted data for weeks 36 to 42 of the testing window to the portion of the testing input timeseries data object that relates to weeks 36 to 42 of the testing window in order to determine a per-iteration accuracy measure for the sixth ordered testing iteration.

In the noted example, after the sixth ordered testing iteration, during a seventh and final ordered testing iteration (i=7), the predictive data analysis computing entity 106 may process the portion of the testing input timeseries data object that relates to weeks 1 to 42 of the testing window to forecast the portion of the testing input timeseries data object that relates to weeks 42 to 48 of the testing window. Afterward, the predictive data analysis computing entity 106 may compare the forecasted data for weeks 42 to 48 of the testing window to the portion of the testing input timeseries data object that relates to weeks 42 to 48 of the testing window in order to determine a per-iteration accuracy measure for the seventh ordered testing iteration.

Thereafter, the predictive data analysis computing entity 106 may combine each per-interaction accuracy measure for each of the seven ordered testing iterations to generate a final accuracy measure. Moreover, the predictive data analysis computing entity 106 may determine that the ARIMA model has a positive validation determination if the accuracy measure of the ARIMA model satisfies an accuracy measure threshold.

At step/operation 406, the predictive data analysis computing entity 106 determines whether the validation determination describes a positive validation determination (i.e., a validation determination describing successful validation/testing of the trained ARIMA model). At step/operation 407, in response to determining that the validation determination describes a positive validation determination, the predictive data analysis computing entity 106 adopts the trained ARIMA model as a validated model until a subsequent training of the ARIMA model (which may be triggered in response to receiving new raw input data entries). In some embodiments, in response to determining that the validation determination describes a positive validation determination, the predictive data analysis computing entity 106 enables use of the trained ARIMA model to generate time-lagged predictions (as described in relation to FIG. 11).

At step/operation 408, in response to determining that the validation determination describes a negative validation determination (i.e., a validation determination describing unsuccessful validation/testing of the trained ARIMA model), the predictive data analysis computing entity 106 refuses to adopt the trained ARIMA model as a validated model and may optionally seek to retrain the ARIMA model using new hyper-parameters.

B. Performing Predictive Inferences Using a Trained ARIMA Model

FIG. 11 is a flowchart diagram of an example process 1100 for performing a predictive inference using a trained ARIMA model. Via the various steps/operations of the process 1100, the predictive data analysis computing entity 106 can utilize a trained ARIMA model (e.g., a trained ARIMA model generated using process 400 of FIG. 4) to efficiently and effectively perform seasonally-adjusted predictions.

The process 1100 begins at step/operation 1101 when the predictive data analysis computing entity 106 identifies an input timeseries data object for a prediction window. For example, the predictive data analysis computing entity 106 may receive an input timeseries data object that describes per-week flu patient percentages for a particular geographic region during the last two years. In this example, the noted per-week flu patient percentages may be determined based at least in part on the medical claim data (e.g., health insurance claim data) associated with the particular geographic region during the predefined number of weeks.

At step/operation 1102, the predictive data analysis computing entity 106 processes the input timeseries data object using the trained ARIMA model to determine one or more prospective time-lagged predictions. In some embodiments, the trained ARIMA model is associated with one or more covariates that describe prospective time-lagged properties of an observed phenomenon. The predictive data analysis computing entity 106 may determine the one or more prospective time-lagged predictions based at least in part on the values of the covariates, where the values of the covariates are determined by processing the input timeseries data object using the noted trained ARIMA model in order to find optimal values for the noted covariates.

For example, given the trained ARIMA model of the equation $FLU2_t = 0.3647 + 0.6694*AR1 + 0.0676*AR2 + 11.6575*FLU2t\{t,i=t+1\} - 11.3916*FLU2t\{t, i=t+2\} - 0.1867*FLU2t\{t, i=t+3\}$ that was described above, the predictive data analysis computing entity 106 may determine a first prospective time-lagged prediction based at least in part on the inferred value for $FLU2t\{t,i=t+1\}$, a second prospective time-lagged prediction based at least in part on the inferred value for $FLU2t\{t,i=t+2\}$, and a third prospective time-lagged prediction based at least in part on the inferred value for $FLU2t\{t,i=t+3\}$.

At step/operation 1103, the predictive data analysis computing entity 106 generates a seasonality component for each prospective time-lagged prediction. In some embodiments, to generate a seasonality component for a prospective time-lagged prediction, the predictive data analysis computing entity 106 determines the temporal position of the inferior time unit of the prospective time-lagged prediction within a superior time period (e.g., determines that a particular prospective time-lagged prediction is associated with week $21^{st}$ of the year) and determines the seasonality component of the noted temporal position based at least in part on the seasonality component of the training input timeseries data object used to generate the trained ARIMA model (e.g., the seasonality component generated at step/operation 802).

At step/operation 1104, the predictive data analysis computing entity 106 adjusts each prospective time-lagged prediction based at least in part on the seasonality component for the prospective time-lagged prediction in order to generate an adjusted prospective time-lagged prediction for each prospective time-lagged prediction. In some embodiments, to adjust each prospective time-lagged prediction based at least in part on the seasonality component for the prospective time-lagged prediction, the predictive data analysis computing entity 106 adds the seasonality component for the prospective time-lagged prediction to the prospective time-lagged prediction.

At step/operation 1105, the predictive data analysis computing entity 106 performs one or more prediction-based actions based at least in part on each adjusted time-lagged prediction. In some embodiments, the predictive data analysis computing entity 106 determines that at least one adjusted time-lagged prediction (e.g., the two-week-lagged prediction) describes a high likelihood of an undesirable event (e.g., high degree of spread of an infectious disease such as influenza) and causes generation of notifications to servers associated with responsible institutions. Other examples of prediction-based actions include automatic load balancing operations (e.g., automatic testing center load balancing operations), automatic resource allocation operations, and/or the like.

In some embodiments, in the context of predicting a likely spread of an infectious disease, the prediction-based actions performed by the predictive data analysis computing entity 106 can cause health officials to mobilize resources, people in at-risk areas to get vaccinated and quarantined, providers (e.g., medical practitioners, clinics, hospitals, and/or the like) to prepare for influx of disease-related cases, employers to take steps to ensure business continuity, and individuals to comply with warnings relevant to their area.

In some embodiments, performing the prediction-based actions comprises enabling display of a prediction output user interface that displays at least some of the adjusted time-lagged predictions for a current time period. An operational example of such a prediction output user interface 1200 is provided in FIG. 12. As depicted in FIG. 12, the prediction output user interface includes a next-week influenza spread prediction 1201 for the geographic region 1210, a two-week-from-now influenza spread prediction 1202 for the geographic region 1210, and a three-week-from-now influenza spread prediction 1202 for the geographic region 1210.

VI. Conclusion

Many modifications and other embodiments will come to mind to one skilled in the art to which this disclosure pertains having the benefit of the teachings presented in the foregoing descriptions and the associated drawings. Therefore, it is to be understood that the disclosure is not to be limited to the specific embodiments disclosed and that modifications and other embodiments are intended to be included within the scope of the appended claims. Although specific terms are employed herein, they are used in a generic and descriptive sense only and not for purposes of limitation.

The invention claimed is:

1. A computer-implemented method comprising:
    identifying, by one or more processors, a seasonally-adjusted training input timeseries data object and a seasonally-adjusted testing timeseries data object for a superior time period within a monitored period, wherein the seasonally-adjusted training input timeseries data object is identified by replacing an outlier value corresponding to an inferior time period within the superior time period with an average value across one or more preceding inferior time periods corresponding to the inferior time period and preceding the superior time period;
    updating, by the one or more processors, a trained autoregressive integrated moving average (ARIMA) machine learning model using the seasonally-adjusted training input timeseries data object by:
        determining an optimal differencing order hyper-parameter of the trained ARIMA machine learning model that is configured to transform the seasonally-adjusted training input timeseries data object into a stationary seasonally-adjusted training input timeseries data object,
        determining an optimal lag order hyper-parameter of the trained ARIMA machine learning model and an optimal moving average order hyper-parameter of the trained ARIMA machine learning model that are collectively configured to optimize a machine learning model utility measure for the trained ARIMA machine learning model, and
        determining one or more optimal parameters of the trained ARIMA machine learning model that are configured to enable the trained ARIMA machine learning model to describe the seasonally-adjusted training input timeseries data object given the optimal differencing order hyper-parameter, the optimal lag order hyper-parameter, and the optimal moving average order hyper-parameter;
    determining a validation determination for the trained ARIMA machine learning model based at least in part on the seasonally-adjusted testing timeseries data object; and
    in response to the validation determination satisfying an accuracy measure threshold, enabling, by the one or more processors, performance of a predictive inference using the trained ARIMA machine learning model in order to generate one or more prospective time-lagged predictions and to perform one or more prediction-based actions based at least in part on the one or more prospective time-lagged predictions.

2. The computer-implemented method of claim 1, wherein identifying the seasonally-adjusted training input timeseries data object comprises:
    for each training time period of a plurality of training time periods in a training window, determining a raw training input value of a plurality of raw training input values associated with a raw training input timeseries data object;
    performing seasonal averaging outlier replacement on the plurality of raw training input values to generate a plurality of seasonally averaged training input values;
    performing logarithmic variance stabilization on the plurality of seasonally averaged training input values in order to generate a transformed training input timeseries data object;
    determining a trend component, a seasonality component, and an error component for the raw training input timeseries data object; and
    determining the seasonally-adjusted training input timeseries data object based at least in part on the trend component and the error component.

3. The computer-implemented method of claim 1, wherein identifying the seasonally-adjusted testing timeseries data object comprises:
    for each testing time period of a plurality of testing time periods in a testing window, determining a raw testing input value of a plurality of raw testing input values associated with a raw testing timeseries data object;
    performing seasonal averaging outlier replacement on the plurality of raw testing input values to generate a plurality of seasonally averaged testing input values;
    performing logarithmic variance stabilization on the plurality of seasonally averaged testing input values in order to generate a transformed testing timeseries data object;
    determining a trend component, a seasonality component, and an error component for the raw testing timeseries data object; and
    determining the seasonally-adjusted testing timeseries data object based at least in part on the trend component and the error component.

4. The computer-implemented method of claim 1, wherein the machine learning model utility measure is determined based at least in part on at least one of an Akaike information criterion measure, a corrected Akaike information criterion measure, and a Bayesian information criterion measure.

5. The computer-implemented method of claim 1, wherein the one or more prospective time-lagged predictions are determined based at least in part on inferred covariates of the trained ARIMA machine learning model.

6. The computer-implemented method of claim 1, wherein the one or more prospective time-lagged predictions comprise at least one of a prospective one-week-lagged prediction, a prospective two-week-lagged prediction, and a prospective three-week-lagged prediction.

7. The computer-implemented method of claim 1, wherein the trained ARIMA machine learning model is a trained seasonal ARIMA machine learning model.

8. The computer-implemented method of claim 1, wherein determining the validation determination comprises:
identifying a plurality of training periods associated with the seasonally-adjusted testing timeseries data object, wherein the plurality of training periods are associated with a training period order;
for each subset of the seasonally-adjusted testing timeseries data object that is associated with an ordered portion of the plurality of training periods, determining an inferred prediction for a subsequent training period of the plurality of training periods by processing the subset of the seasonally-adjusted testing timeseries data object using the trained ARIMA machine learning model; and
determining the validation determination based at least in part on the seasonally-adjusted testing timeseries data object and each inferred prediction determined based at least in part on a subset of the seasonally-adjusted testing timeseries data object.

9. The computer-implemented method of claim 1, wherein the one or more prospective time-lagged predictions describe one or more influenza outbreak predictions.

10. The computer-implemented method of claim 9, wherein performing the one or more prediction-based actions comprises generating an influenza outbreak prediction user interface object for one or more prospective time-lagged periods based at least in part on the one or more influenza outbreak predictions.

11. A system comprising a memory and one or more processors configured:
identify a seasonally-adjusted training input timeseries data object and a seasonally-adjusted testing timeseries data object for a superior time period within a monitored period, wherein the seasonally-adjusted training input timeseries data object is identified by replacing an outlier value corresponding to an inferior time period within the superior time period with an average value across one or more preceding inferior time periods corresponding to the inferior time period and preceding the superior time period;
update a trained autoregressive integrated moving average (ARIMA) machine learning model using the seasonally-adjusted training input timeseries data object by:
  determining an optimal differencing order hyper-parameter of the trained ARIMA machine learning model that is configured to transform the seasonally-adjusted training input timeseries data object into a stationary seasonally-adjusted training input timeseries data object,
  determining an optimal lag order hyper-parameter of the trained ARIMA machine learning model and an optimal moving average order hyper-parameter of the trained ARIMA machine learning model that are collectively configured to optimize a machine learning model utility measure for the trained ARIMA machine learning model, and
  determining one or more optimal parameters of the trained ARIMA machine learning model that are configured to enable the trained ARIMA machine learning model to describe the seasonally-adjusted training input timeseries data object given the optimal differencing order hyper-parameter, the optimal lag order hyper-parameter, and the optimal moving average order hyper-parameter;
determine a validation determination for the trained ARIMA machine learning model based at least in part on the seasonally-adjusted testing timeseries data object; and
in response to the validation determination satisfying an accuracy measure threshold, enable performance of a predictive inference using the trained ARIMA machine learning model in order to generate one or more prospective time-lagged predictions and to perform one or more prediction-based actions based at least in part on the one or more prospective time-lagged predictions.

12. The system of claim 11, wherein identifying the seasonally-adjusted training input timeseries data object comprises:
for each training time period of a plurality of training time periods in a training window, determining a raw training input value of a plurality of raw training input values associated with a raw training input timeseries data object;
performing seasonal averaging outlier replacement on the plurality of raw training input values to generate a plurality of seasonally averaged training input values;
performing logarithmic variance stabilization on the plurality of seasonally averaged training input values in order to generate a transformed training input timeseries data object;
determining a trend component, a seasonality component, and an error component for the raw training input timeseries data object; and
determining the seasonally-adjusted training input timeseries data object based at least in part on the trend component and the error component.

13. The system of claim 11, wherein identifying the seasonally-adjusted testing timeseries data object comprises:
for each testing time period of a plurality of testing time periods in a testing window, determining a raw testing input value of a plurality of raw testing input values associated with a raw testing timeseries data object;
performing seasonal averaging outlier replacement on the plurality of raw testing input values to generate a plurality of seasonally averaged testing input values;
performing logarithmic variance stabilization on the plurality of seasonally averaged testing input values in order to generate a transformed testing timeseries data object;
determining a trend component, a seasonality component, and an error component for the raw testing timeseries data object; and
determining the seasonally-adjusted testing timeseries data object based at least in part on the trend component and the error component.

14. The system of claim 11, wherein determining the validation determination comprises:
identifying a plurality of training periods associated with the seasonally-adjusted testing timeseries data object, wherein the plurality of training periods are associated with a training period order;

for each subset of the seasonally-adjusted testing timeseries data object that is associated with an ordered portion of the plurality of training periods, determining an inferred prediction for a subsequent training period of the plurality of training periods by processing the subset of the seasonally-adjusted testing timeseries data object using the trained ARIMA machine learning model; and determining the validation determination based at least in part on the seasonally-adjusted testing timeseries data object and each inferred prediction determined based at least in part on a subset of the seasonally-adjusted testing timeseries data object.

15. The system of claim 11, wherein the one or more prospective time-lagged predictions describe one or more influenza outbreak predictions.

16. At least one non-transitory computer-readable storage media including instructions that, when executed by one or more processors, cause the one or more processors to:

identify a seasonally-adjusted training input timeseries data object and a seasonally-adjusted testing timeseries data object for a superior time period within a monitored period, wherein the seasonally-adjusted training input timeseries data object is identified by replacing an outlier value corresponding to an inferior time period within the superior time period with an average value across one or more preceding inferior time periods corresponding to the inferior time period and preceding the superior time period;

update a trained autoregressive integrated moving average (ARIMA) machine learning model using the seasonally-adjusted training input timeseries data object by:

determining an optimal differencing order hyper-parameter of the trained ARIMA machine learning model that is configured to transform the seasonally-adjusted training input timeseries data object into a stationary seasonally-adjusted training input timeseries data object, determining an optimal lag order hyper-parameter of the trained ARIMA machine learning model and an optimal moving average order hyper-parameter of the trained ARIMA machine learning model that are collectively configured to optimize a machine learning model utility measure for the trained ARIMA machine learning model, and determining one or more optimal parameters of the trained ARIMA machine learning model that are configured to enable the trained ARIMA machine learning model to describe the seasonally-adjusted training input timeseries data object given the optimal differencing order hyper-parameter, the optimal lag order hyper-parameter, and the optimal moving average order hyper-parameter;

determine a validation determination for the trained ARIMA machine learning model based at least in part on the seasonally-adjusted testing timeseries data object; and in response to the validation determination satisfying an accuracy measure threshold, enable performance of a predictive inference using the trained ARIMA machine learning model in order to generate one or more prospective time-lagged predictions and to perform one or more prediction-based actions based at least in part on the one or more prospective time-lagged predictions.

17. The at least one non-transitory computer-readable storage media of claim 16, wherein identifying the seasonally-adjusted training input timeseries data object comprises:

for each training time period of a plurality of training time periods in a training window, determining a raw training input value of a plurality of raw training input values associated with a raw training input timeseries data object;

performing seasonal averaging outlier replacement on the plurality of raw training input values to generate a plurality of seasonally averaged training input values;

performing logarithmic variance stabilization on the plurality of seasonally averaged training input values in order to generate a transformed training input timeseries data object;

determining a trend component, a seasonality component, and an error component for the raw training input timeseries data object; and determining the seasonally-adjusted training input timeseries data object based at least in part on the trend component and the error component.

18. The at least one non-transitory computer-readable storage media of claim 16, wherein identifying the seasonally-adjusted testing timeseries data object comprises:

for each testing time period of a plurality of testing time periods in a testing window, determining a raw testing input value of a plurality of raw testing input values associated with a raw testing timeseries data object;

performing seasonal averaging outlier replacement on the plurality of raw testing input values to generate a plurality of seasonally averaged testing input values;

performing logarithmic variance stabilization on the plurality of seasonally averaged testing input values in order to generate a transformed testing timeseries data object;

determining a trend component, a seasonality component, and an error component for the raw testing timeseries data object; and determining the seasonally-adjusted testing timeseries data object based at least in part on the trend component and the error component.

19. The at least one non-transitory computer-readable storage media of claim 16, wherein determining the validation determination comprises:

identifying a plurality of training periods associated with the seasonally-adjusted testing timeseries data object, wherein the plurality of training periods are associated with a training period order;

for each subset of the seasonally-adjusted testing timeseries data object that is associated with an ordered portion of the plurality of training periods, determining an inferred prediction for a subsequent training period of the plurality of training periods by processing the subset of the seasonally-adjusted testing timeseries data object using the trained ARIMA machine learning model; and determining the validation determination based at least in part on the seasonally-adjusted testing timeseries data object and each inferred prediction determined based at least in part on a subset of the seasonally-adjusted testing timeseries data object.

20. The at least one non-transitory computer-readable storage media of claim 16, wherein the one or more prospective time-lagged predictions describe one or more influenza outbreak predictions.

* * * * *